United States Patent [19]

Katagiri et al.

[11] Patent Number: 4,548,886
[45] Date of Patent: Oct. 22, 1985

[54] RADIATION SENSITIVE ORGANIC THIN FILM COMPRISING AN AZULENIUM SALT

[75] Inventors: Kazuharu Katagiri; Yoshihiro Oguchi, both of Yokohama; Yoshio Takasu, Tama, all of Japan

[73] Assignee: Canon Kabushiki Kaisha, Tokyo, Japan

[21] Appl. No.: 500,978

[22] Filed: Jun. 3, 1983

[30] Foreign Application Priority Data

| Jun. 8, 1982 | [JP] | Japan | 57-98047 |
| Sep. 13, 1982 | [JP] | Japan | 57-160156 |
| Sep. 13, 1982 | [JP] | Japan | 57-160157 |
| Sep. 22, 1982 | [JP] | Japan | 57-165263 |
| Jan. 17, 1983 | [JP] | Japan | 58-6070 |
| Jan. 20, 1983 | [JP] | Japan | 58-7523 |

[51] Int. Cl.$^4$ ............................................. G03G 5/06
[52] U.S. Cl. ........................................ 430/70; 430/57; 430/71; 430/73; 430/945
[58] Field of Search .................. 430/70, 71, 73, 57

[56] References Cited

U.S. PATENT DOCUMENTS

| 3,397,086 | 8/1968 | Bartfai | 117/218 |
| 3,816,118 | 6/1974 | Byrne | 96/1.5 |
| 3,898,083 | 8/1975 | Hillegas | 96/1.5 |
| 4,251,613 | 2/1981 | Sasaki | 430/72 |
| 4,278,747 | 7/1981 | Murayama et al. | 430/73 |
| 4,315,983 | 2/1982 | Kawamura | 430/70 |

OTHER PUBLICATIONS

Research Disclosure No. 20517, (May, 1981).
V. B. Jipson and C. R. Jones, J. Vac. Sci. Technol. 18(1), Jan./Feb. 1981, pp. 105–109.
R.C.A. Review, An Organic Photoconductive System by H. G. Grieg, vol. 23, pp. 413–419, Sep. 1962.

*Primary Examiner*—John L. Goodrow
*Attorney, Agent, or Firm*—Fitzpatrick, Cella Harper & Scinto

[57] ABSTRACT

A radiation sensitive organic thin film comprising a compound which has at least one nucleus of azulanium salt.

34 Claims, 7 Drawing Figures

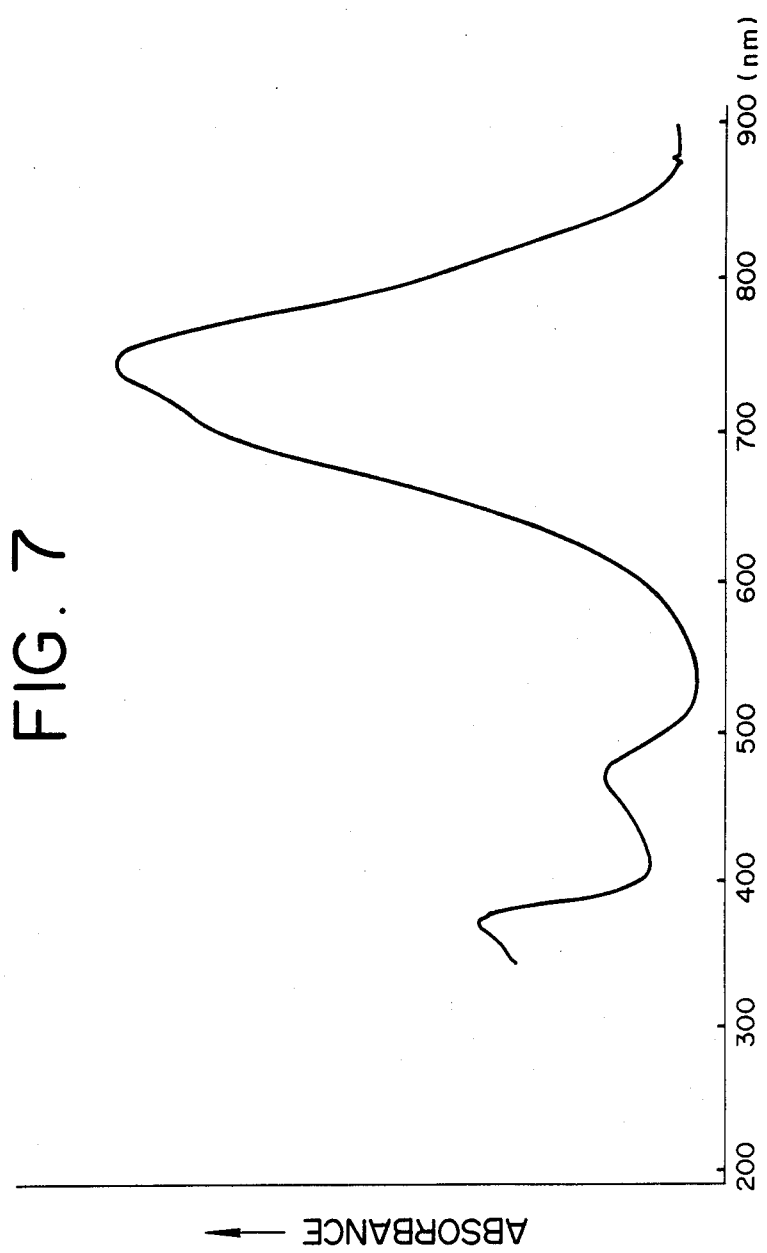

RADIATION SENSITIVE ORGANIC THIN FILM COMPRISING AN AZULENIUM SALT

BACKGROUND OF THE INVENTION

1. Field of the Invention

This invention relates to organic coating films which effectively absorb radiation, especially lasers of relatively long wavelengths, to convert into other energy. More particularly, it relates to a novel organic coating film suitable as: a photosensitive film for use in an electrophotographic printer which employs a semiconductor laser as light source; an optical disc coating film which permits the writing and reproduction of information with a semiconductor laser; an infrared ray cutting filter; and so forth.

2. Description of the Prior Art

The electrophotographic printing system employing a laser as a light source reproduces a given information image by modulating the laser beam with electric signals in response to the original information image, and scanning a photosensitive surface with the modulated laser beam by means of a galvano-mirror or the like to form an electrostatic latent image, followed by toner development and transferring. Gas lasers such as a helium-cadmium laser (wavelength 441.6 nm) and a helium-neon laser (wavelength 632.8 nm) have been generally used in this printing system. The photosensitive members for these light sources are therefore satisfactory if spectral-sensitized up to around 650 nm (sensitized to operate effectively to rays of wavelengths up to around 650 nm). Such photosensitive members so far known include those (1) employing a charge transfer complex of polyvinylcarbazole with trinitrofluorenone in the photosensitive layer, (2) employing a vapor-deposited layer of tellurium sensitized with selenium as a photosensitive layer, (3) employing a photosensitive layer comprising two vapor-deposited films, one being a selenium film formed as a charge transport layer on a conductive layer and the other being a selenium-tellurium film formed on said selenium film, (4) employing cadmium sulfide, as a photosensitive layer, spectral-sensitized with a sensitizing colorant, and (5) employing two photosensitive layers functioning as a charge generation layer containing organic pigments and a charge transport layer, respectively, both spectral-sensitized up to a required longer wavelength.

The optical disc coating film can store high density information in the form of spiral or circular tracks of fine pits (e.g. about 1µ) optically detectable. For writing information on the disc, the surface of a laser-sensitive layer on the disc is scanned spirally or circularly with a converged laser beam modulated, thereby forming pits at the spots irradiated with pulses of the laser beam. The laser-sensitive layer can form optically detectable pits by absorbing energy of the laser. According to a heat-mode recording technique, for instance, a laser-sensitive layer absorbs thermal energy of the laser and forms small depressions (pits) by evaporation or fusing at the sites that have absorbed the thermal energy. According to another heat-mode recording technique, pits having an optically detectable density are formed at the spots which have absorbed laser energy.

The information stored on the optical disc can be read by scanning the disc surface along the track with a laser and detecting optical differences between the pits and the pit-free area. For instance, a laser is irradiated to scan the disc surface along the track and the laser energy reflected from the disc is monitored with a photodetector. When the pit-free site is irradiated, the output of the photodetector is low; when the pit is irradiated, the laser is reflected sufficiently from an underlying reflecting interface, thereby increasing the output of the photodetector.

For the recording medium to be used in this type of light, materials composed mainly of inorganic substances have been proposed until now, including thin metallic films such as aluminum vapor-deposited films, thin bismuth films, thin tellulium oxide films, and amorphous glass films of chalcogenite group compounds.

In recent years, there have been developed semiconductor laser devices of small size and low cost. Further lasers emitted from these devices can be directly modulated. However, most of these lasers have a wavelength of at least 750 nm. Accordingly, in order to carry out recording and/or reproduction with such a long-wavelength semiconductor laser, the laser-sensitive film used should have an absorption maximum in a long wavelength region generally of 750–850 nm.

However, existing laser-sensitive films, in particular those composed mainly of inorganic materials, have high reflectance for laser beams, and hence exhibit lower efficiency of laser energy utilization and poor sensitivity characteristics. In addition, extension of the response-wavelength region of these films to 750 nm or longer is disadvantageous, since these laser-sensitive films become complicated in layer construction and in particular when these sensitized films are used electrophotographic applications, the sensitizing dyes will be faded by repeated charging and exposing operations.

Such being the case, there have been proposed in recent years organic films highly sensitive to rays of wavelengths of 750 nm and longer. Examples of such organic flims are those containing a pyrylium dye disclosed in U.S. Pat. No. 4,315,983 and "Research Disclosure" No. 20517 (May, 1981) and those containing a squarylium dye disclosed in J. Vac. Sci. Technol., 18 (1), 105–109 (January/February, 1981).

Besides these, a report on the photoconductivity of phthalocyanine pigments was presented in "RCA Review", Vol. 23, 413–419 (September 1962). Electrophotographic photosensitive members employing phthalocyanine pigments were disclosed in U.S. Pat. Nos. 3,397,086 and 3,816,118. Further, disazo pigmentcontaining films disclosed in U.S. Pat. Nos. 3,898,084 and 4,251,613 are also known as an example of laser-sensitive organic films.

However, organic compounds having absorption maxima in the longer wavelength region are, as a rule, the more unstable, often decomposing with a slight increase in temperature. In view of these problems and additionally of various characteristics required for use in electrophotographic printers or in optical discs, organic films sensitive to long wavelength rays, hitherto proposed are not necessarily satisfactory for practical use.

These organic semiconductive materials are easy to synthesize as compared with inorganic semiconductive materials, and a compound sensitive to rays of required wavelengths can be synthesized. Electrophotographic photosensitive members having a film of such an organic semiconductive material on a conductive substrate have an advantage in better sensitivity to color. However, little organic semiconductive materials can be used with respect to sensitivity and durability in practice. Further, there have been developed in recent years organic semiconductive materials having high sensitivity characteristics to long wave length rays of 700 nm or longer accompanying the development of low output semiconductor laser. However, there has been found no organic semiconductive material having the satisfactory characteristics.

SUMMARY OF THE INVENTION

The first object of this invention is to provide a novel and useful organic coating film.

The second object of this invention is to provide an organic coating film having an absorption band in a long wavelength region, particularly at 750 nm or longer.

The third object of this invention is to provide an organic coating film stable to heat.

The fourth object of this invention is to provide an electrophotographic photosensitive coating film for use in electrophotographic printers employing a laser as a light source.

The fifth object of this invention is to provide an electrophotographic photosensitive coating film highly sensitive to a ray of wavelength 750 nm or longer.

The sixth object of this invention is to provide a coating film useful for optical disc recording.

The seventh object of this invention is to provide an optical disc recording film highly sensitive to a ray of wavelength 750 nm or longer and satisfactory in S/N ratio.

The eighth object of this invention is to provide a novel organic semiconductive material.

The ninth object of this invention is to provide a novel organic semiconductive film.

The tenth object of this invention is to provide an electrophotographic photosensitive member employing a novel organic semiconductive film.

The 11th object of this invention is to provide an electrophotographic photosensitive member suited to electrophotographic copying machines.

The 12th object of this invention is to provide an electrophotographic photosensitive member suited to laser-beam-scanning electrophotographic printers.

The 13th object of this invention is to provide an electrophotographic photosensitive member highly sensitive to rays of long wavelengths.

These objects of this invention are achieved with a radiation-sensitive organic thin film comprising a compound which has at least one nucleus of an azulenium salt.

BRIEF DESCRIPTION OF THE DRAWINGS

FIGS. 6 and 7 are illustrations of visible-infrared absorption spectra of the compound Nos. 78 and 76, respectively, in dichloromethane.

DETAILED DESCRIPTION OF THE PREFERRED EMBODIMENTS

Figure 1:
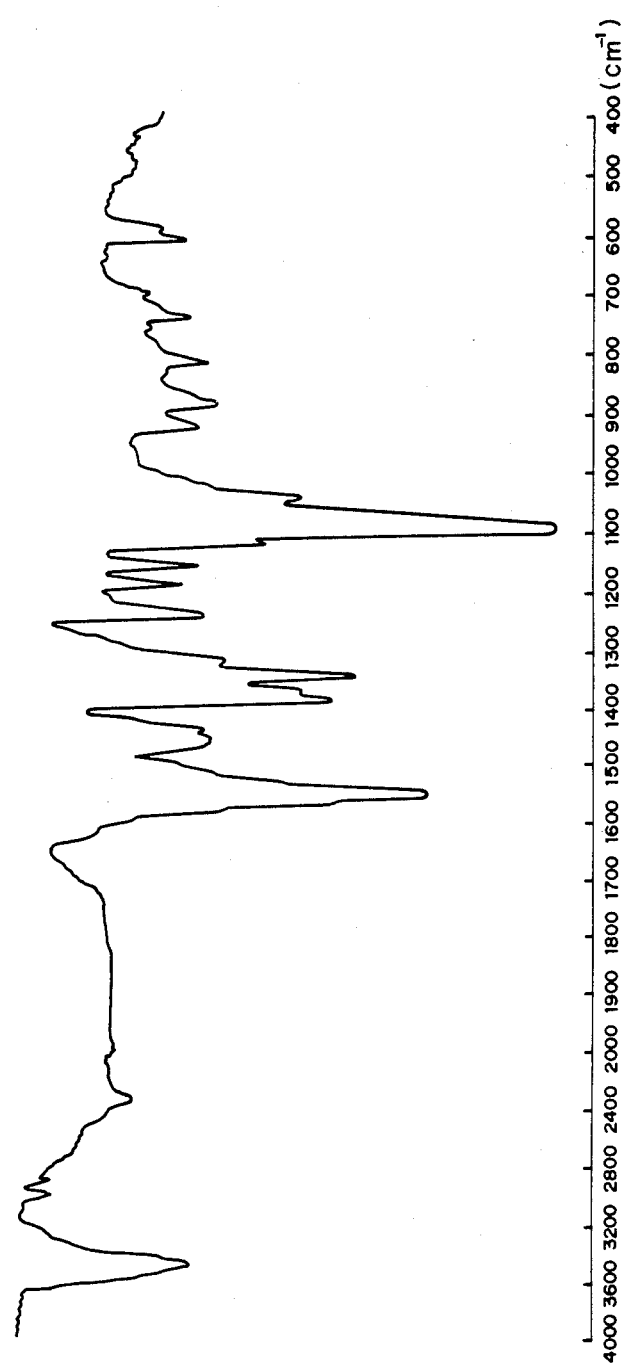
FIG. 1 illustrates an infrared spectrum of the compound No. 54 cited later.

In preferred embodiments of this invention, the compound having at least one azulenium nucleus is represented by the following general formula I, II, or III:

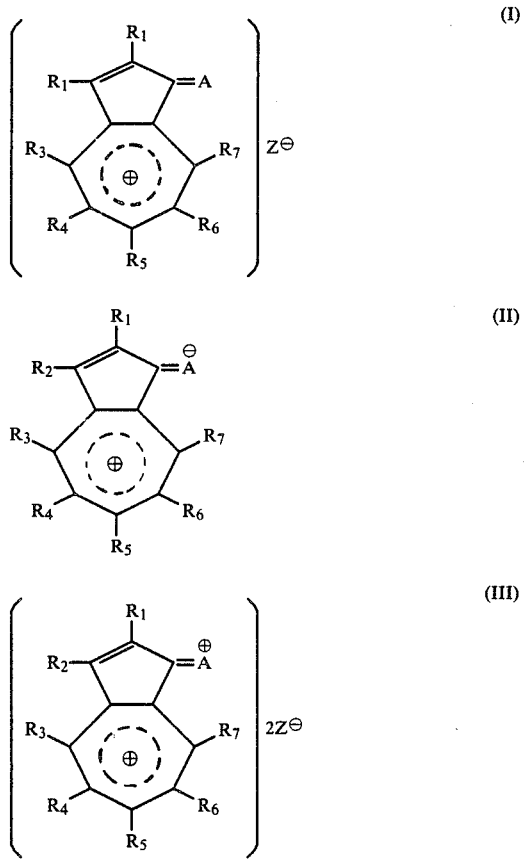

In these formulae, each of $R_1$–$R_7$ represents hydrogen, halogen (e.g. chlorine, bromine, or iodine), or an organic monovalent residue. While the monovalent residue can be selected from a wide variety of radicals, preferred ones thereof are alkyl groups, e.g. methyl, ethyl, n-propyl, isopropyl, n-butyl, t-butyl, n-amyl, n-hexyl, n-octyl, 2-ethylhexyl, and t-octyl; alkoxy groups, e.g. methoxy, ethoxy, propoxy, and butoxy; substituted or unsubstituted aryl groups, e.g. phenyl, tolyl, xylyl, ethylphenyl, methoxyphenyl, ethoxyphenyl, chlorophenyl, nitrophenyl, dimethylaminophenyl, α-naphthyl, and β-naphthyl; substituted or unsubstituted aralkyl groups, e.g. benzyl, 2-phenylethyl, 2-phenyl-1-methylethyl, bromobenzyl, 2-bromophenylethyl, methylbenzyl, methoxybenzyl, and nitrobenzyl; acyl groups, e.g. acetyl, propionyl, butyryl, valeryl, benzoyl, toluoyl, naphthoyl, phthaloyl, and furoyl; substituted or unsubstituted amino groups, e.g. amino, dimethylamino, diethylamino, dipropylamino, acetylamino, and benzoylamino; substituted or unsubstituted styryl groups, e.g. styryl, dimethylaminostyryl, diethylaminostyryl, dipropylaminostyryl, methoxystyryl, ethoxystyryl, and methylstyryl; nitro; hydroxyl; carboxyl; cyano; and substituted or unsubstituted arylazo groups, e.g. phenylazo, α-naphthylazo, β-naphthylazo, dimethylaminophenylazo, chlorophenylazo, nitrophenylazo, methoxyphenylazo, and tolylazo. Of the combinations of $R_1$–$R_2$, $R_3$–$R_4$, $R_4$–$R_5$, $R_5$–$R_6$, and $R_6$–$R_7$, at least one may or may not form a substituted or unsubstituted aromatic ring, e.g. benzene, naphthalene, chlorobenzene, bromobenzene, methylbenzene, ethylbenzene, methoxybenzene, or ethoxybenzene ring.

$Z^\ominus$ represents an anionic residue; A represents an organic divalent residue linked by a double bond to the azulenium skeleton. The azulenium compounds containing said A of this invention can be represented, for example, by the following general formulae 1 to 11: $Q^\oplus$ in the formulae represents the following azulenium skeleton and the right-hand moieties, excluding $Q^\oplus$, in the formulae are represented by A.

Azulenium skeleton ($Q^\oplus$):

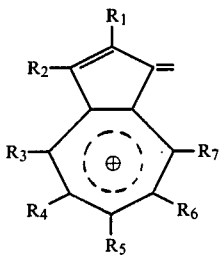

General formula (1):

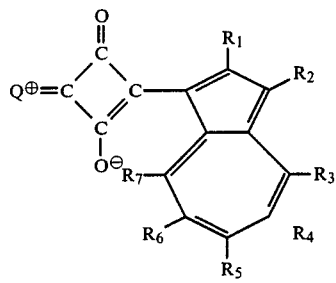

$R_1$ to $R_7$ in this formula are as defined above.
General formula (2):

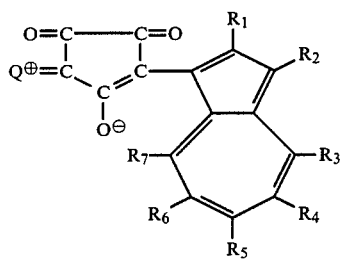

$R_1$ to $R_7$ in this formula are as defined above.
General formula (3):

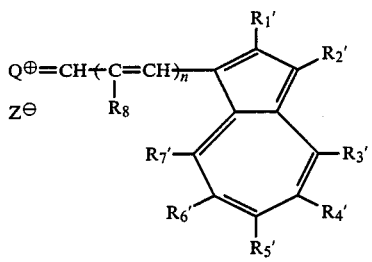

Each of $R_1'$ to $R_7'$ in this formula represents hydrogen, halogen, e.g. chlorine, bromine, or iodine, or an organic monovalent residue, which can be selected from a variety of radicals. Preferred examples of the organic monovalent residues are alkyl groups, e.g. methyl, ethyl, n-propyl, isopropyl, n-butyl, t-butyl, n-amyl, n-hexyl, n-octyl, 2-ethylhexyl, and t-octyl; alkoxy groups, e.g. methoxy, ethoxy, propoxy, and butoxy; substituted or unsubstituted aryl groups, e.g. phenyl, tolyl, xylyl, ethylphenyl, methoxyphenyl, ethoxyphenyl, chlorophenyl, nitrophenyl, dimethylaminophenyl, α-naphthyl, and β-naphthyl; substituted or unsubstituted aralkyl groups, e.g. benzyl, 2-phenylethyl, 2-phenyl-1-methylethyl, bromobenzyl, 2-bromophenylethyl, methylbenzyl, methoxybenzyl, and nitrobenzyl; acyl groups, e.g. acetyl, propionyl, butyryl, valeryl, benzoyl, naphthoyl, phthaloyl, and furoyl; substituted or unsubstituted amino groups, e.g. amino, dimethylamino, diethylamino, dipropylamino, acetylamino, and benzoylamino; substituted or unsubstituted styryl groups, e.g. styryl, dimethylaminostyryl, diethylaminostyryl, dipropylaminostyryl, methoxystyryl, ethoxystyryl, and methylstyryl; nitro; hydroxyl; carboxyl; cyano; and substituted or unsubstituted arylazo groups, e.g. phenylazo, α-naphthylazo, β-naphthylazo, dimethylaminophenylazo, chlorophenylazo, nitrophenylazo, methoxyphenylazo, and tolylazo. Of the combinations of $R_1'$-$R_2'$, $R_3'$-$R_4'$, $R_4'$-$R_5'$, $R_5'$-$R_6'$, and $R_6'$-$R_7'$, at least one may or may not form a substituted or unsubstituted aromatic ring, e.g. benzene, naphthalene, chlorobenzene, bromobenzene, methylbenzene, ethylbenzene, methoxybenzene, or ethoxybenzene. $Z^\ominus$ represents an anionic residue; $R_8$ represents hydrogen, nitro, cyano, or alkyl (e.g. methyl, ethyl, propyl, or butyl), or aryl (e.g. phenyl, tolyl, or xylyl); and n represents an integer of 0, 1, or 2.

General formula (4):

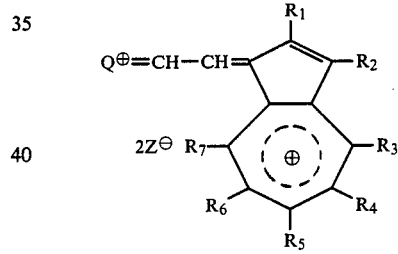

$R_1$ to $R_7$ and $Z^\ominus$ in this formula are as defined above.
General formula (5):

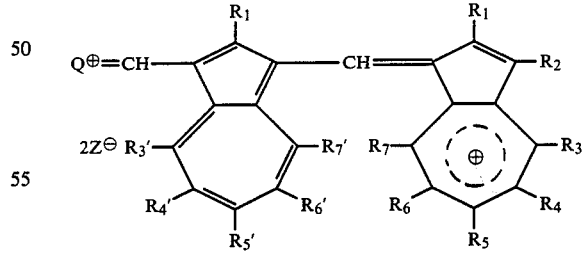

In this formula, $R_1$ to $R_7$, $R_1'$ to $R_7'$, and $Z^\ominus$ are as defined above.
General formula (6):

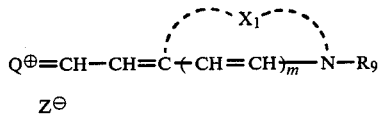

In this formula; $X_1$ represents a non-metal-atomic group necessary to complete a nitrogencontaining heterocyclic ring, e.g. pyridine, thiazole, benzothiazole, naphthothiazole, oxazole, benzoxazole, naphthoxazole, imidazole, benzimidazole, 2-quinoline, 4-quinoline, isoquinoline, or indole ring. This heterocyclic ring may be substituted by halogen, e.g. chlorine, bromine, or iodine; alkyl, e.g. methyl, ethyl, propyl, or butyl; or aryl, e.g. phenyl, tolyl, or xylyl. $R_9$ represents alkyl, e.g. methyl, ethyl, propyl, or butyl; substituted alkyl, e.g. 2-hydroxyethyl, 2-methoxyethyl, 2-ethoxyethyl, 3-hydroxypropyl, 3-methoxypropyl, 3-ethoxypropyl, 3-chloropropyl, 3-bromopropyl, or 3-carboxypropyl; cycloalkyl, e.g. cyclohexyl or cyclopropyl; alkenyl, e.g. allyl; aralkyl, e.g. benzyl, 2-phenylethyl, 3-phenylpropyl, 4-phenylbutyl, α-naphthylmethyl, or β-naphthylmethyl; substituted aralkyl, e.g. methylbenzyl, ethylbenzyl, dimethylbenzyl, trimethylbenzyl, chlorobenzyl, or bromobenzyl; aryl, e.g. phenyl, tolyl, xylyl, α-naphthyl, or β-naphthyl; or substituted aryl, e.g. chlorophenyl, dichlorophenyl, trichlorophenyl, ethylphenyl, methoxyphenyl, dimethoxyphenyl, aminophenyl, nitrophenyl, or hydroxyphenyl. $Z^{\ominus}$ represents an anionic residue; and m represents an integer of 0 or 1.

General formula (7):

In this formula, $R_{10}$ represents substituted or unsubstituted aryl, e.g. phenyl, tolyl, xylyl, biphenyl, α-naphthyl, β-naphthyl, anthryl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidylphenyl, piperazinophenyl, diphenylaminophenyl, acetylaminophenyl, benzoylaminophenyl, acetylphenyl, benzoylphenyl, or cyanophenyl; and $Z^{\ominus}$ represents an anionic residue.

General formula (8):

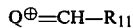

In this formula, $R_{11}$ represents a monovalent heterocyclic residue, e.g. residue of furan, thiophene, benzofran, thionaphthene, dibenzofuran, carbazole, phenothiazine, phenoxazine, or of pyridine; and $Z^{\ominus}$ represents an anionic residue.

General formula (9):

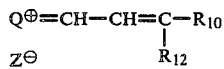

In this formula, $R_{12}$ represents hydrogen; alkyl, e.g. methyl, ethyl, propyl, or butyl; or substituted or unsubstituted aryl, e.g. phenyl, tolyl, xylyl, biphenyl, ethylphenyl, chlorophenyl, methoxyphenyl, ethoxyphenyl, nitrophenyl, aminophenyl, dimethylaminophenyl, diethylaminophenyl, acetylaminophenyl, α-naphthyl, β-naphthyl, anthryl, or pyrenyl; and $R_{10}$ and $Z^{\ominus}$ are as defined above.

General formula (10):

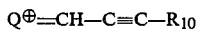

In this formula, $R_{10}$ and $Z^{\ominus}$ are as defined above.
General formula (11):

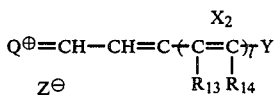

In this formula; $X_2$ represents an atomic group necessary to complete pyrane, thiopyrane, selenopyrane, benzopyrane, benzothiopyrane, benzoselenopyrane, naphthopyrane, naphthothiopyrane, or naphthoselenopyrane ring substituted or unsubstituted; l represents an integer of 0 or 1; Y represents sulfur, oxygen, or selenium; $R_{13}$ and $R_{14}$ each represent hydrogen, alkyl (e.g. methyl, ethyl, propyl, or butyl), alkoxy (e.g. methoxy, ethoxy, propoxy, or butoxy), substituted or unsubstituted aryl (e.g. phenyl, tolyl, xylyl, chlorophenyl, biphenyl, or methoxyphenyl), substituted or unsubstituted styryl (e.g. styryl, p-methylstyryl, o-chlorostyryl, or p-methoxystyryl), ring-substituted or unsubstituted 4-phenyl-1,3-butadienyl (e.g. 4-phenyl-1,3-butadienyl or 4-(p-methylphenyl)-1,3-butadienyl), or a substituted or unsubstituted heterocyclic residue (e.g. quinolyl, pyridyl, carbazolyl, or furyl); and $Z^{\ominus}$ represents an anionic residue.

Examples of $Z^{\ominus}$ in the above general formulae (1)–(11) are perchlorate, fluoroborate, sulfoacetate, iodide, chloride, bromide, p-toluenesulfonate, alkylsulfonates, alkyldisulfonates, benzenedisulfonate, halosulfonates, picrate, tetracyanoethylene, and tetracyanoquinodimethane anionic residues.

Examples of the azulenium compound used in this invention are enumerated below.

Compounds represented by the general formula (1):

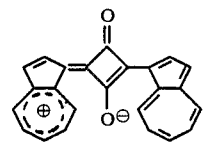

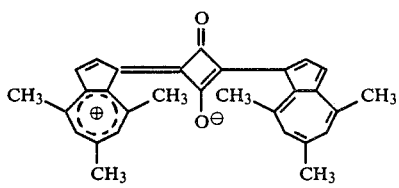

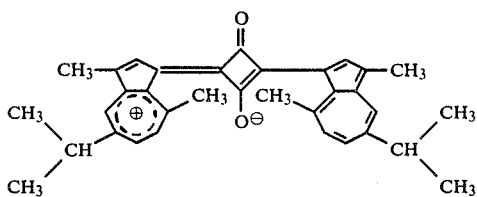

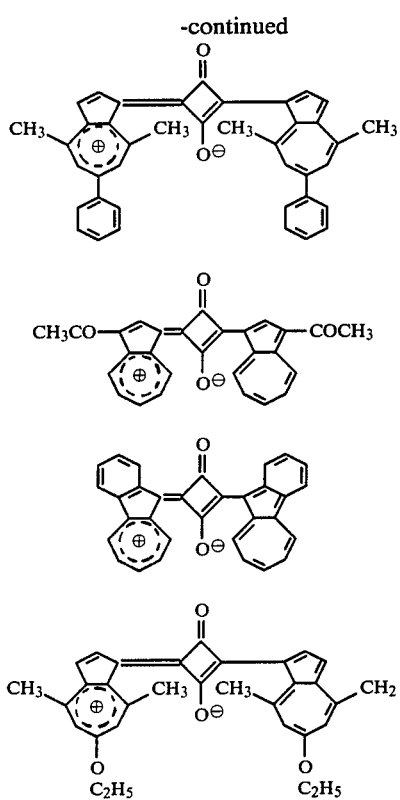

-continued
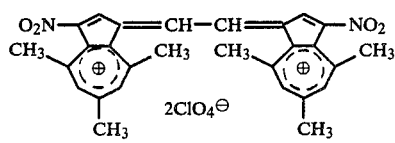 (23)
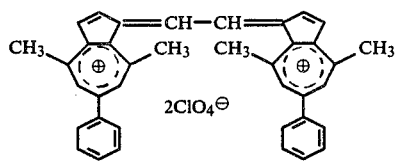 (24)
Compounds represented by the general formula (5):
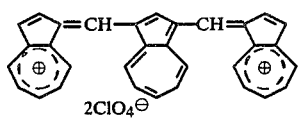 (25)
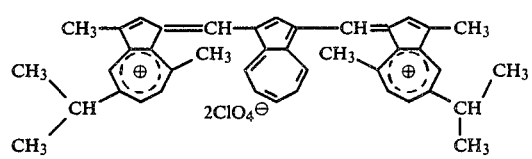 (26)
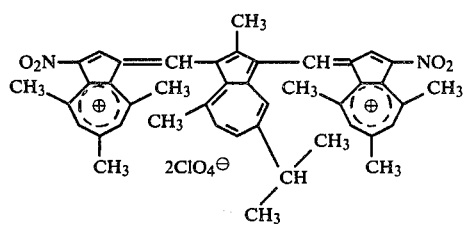 (27)
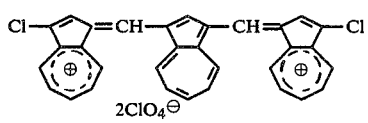 (28)
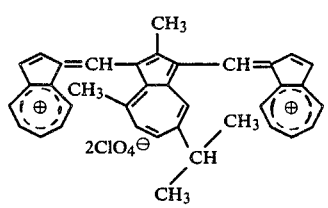 (29)
Compounds represented by the general formula (6):
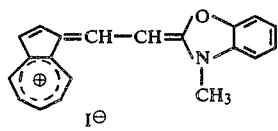 (30)
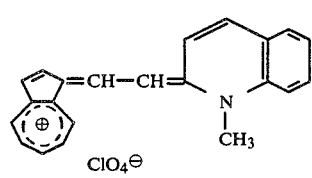 (31)
-continued
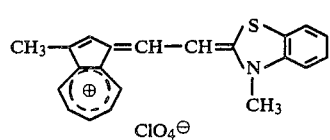 (32)
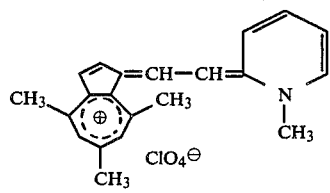 (33)
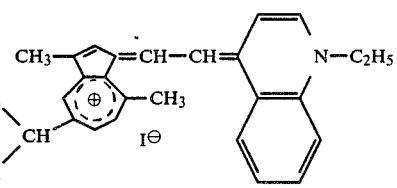 (34)
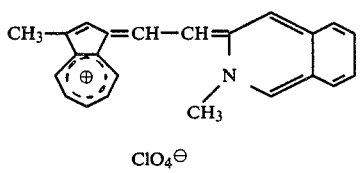 (35)
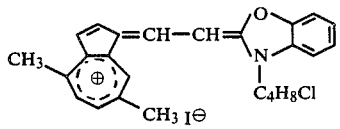 (36)
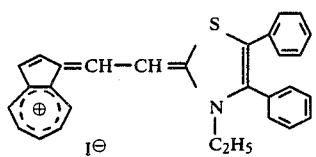 (37)
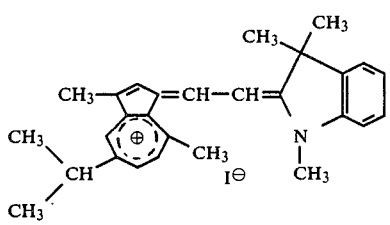 (38)
Compounds represented by the general formula (7):
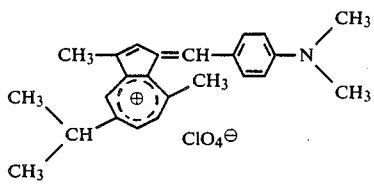 (39)

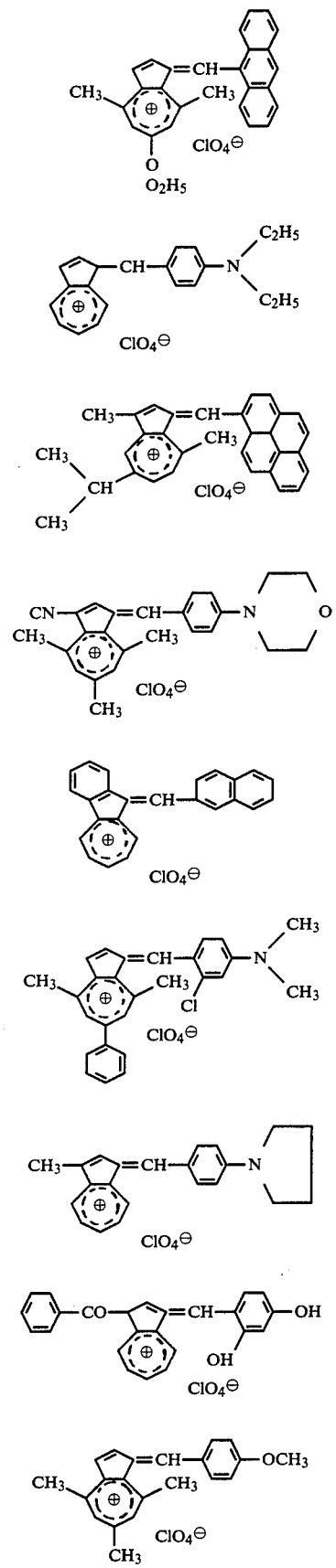
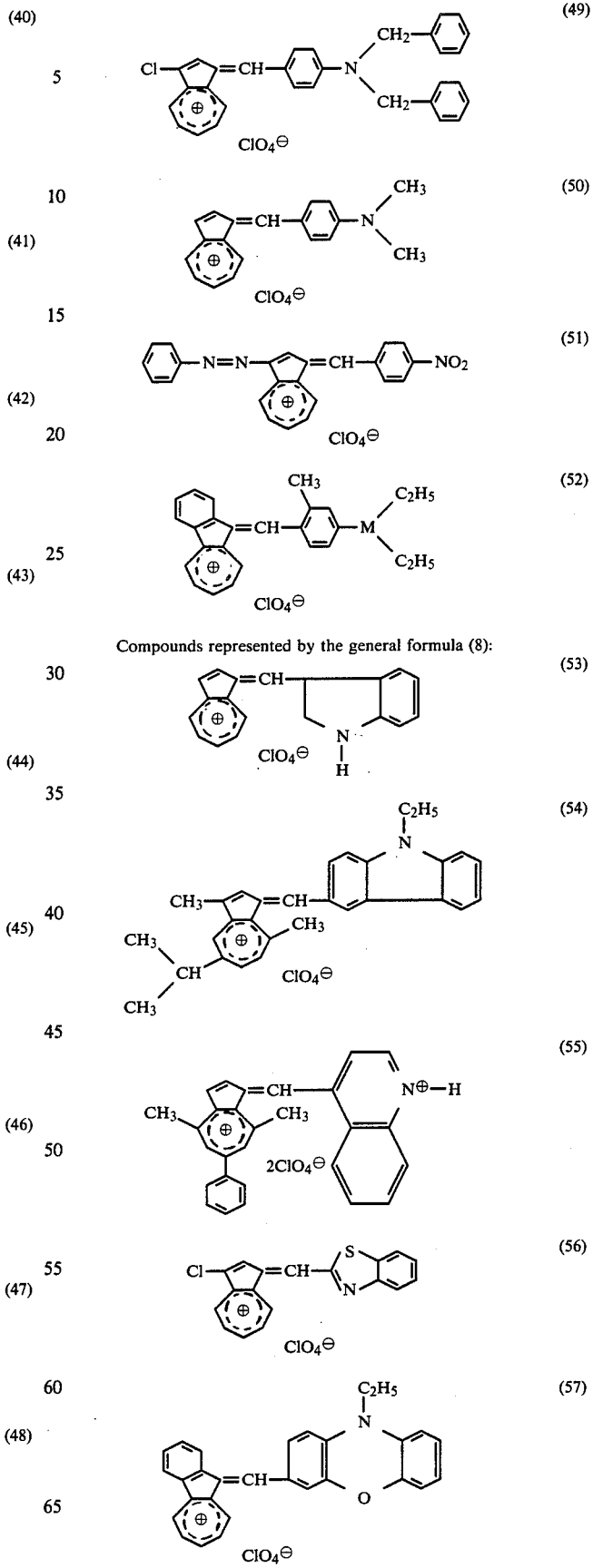
Compounds represented by the general formula (8):

-continued
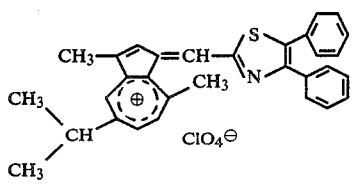 (58)
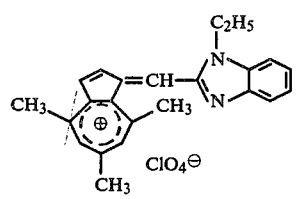 (59)
Compounds represented by the general formula (9):
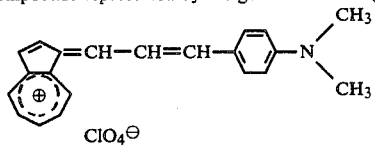 (60)
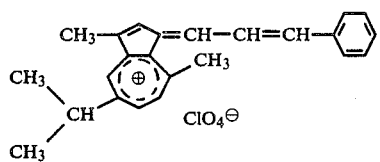 (61)
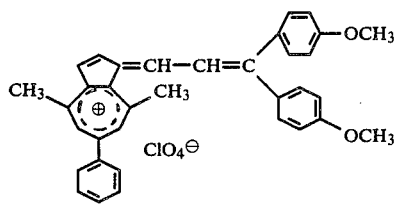 (62)
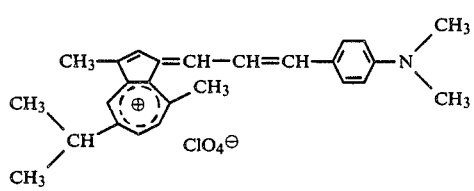 (63)
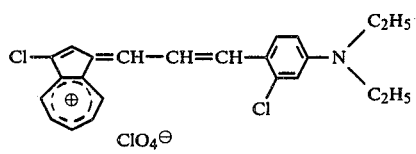 (64)
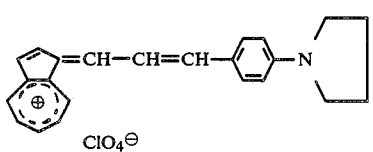 (65)
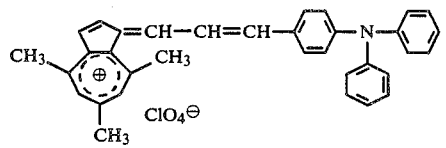 (66)
-continued
Compounds represented by the general formula (10):
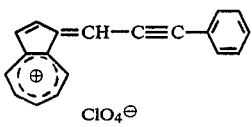 (67)
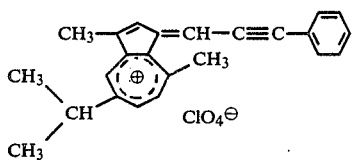 (68)
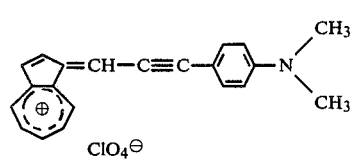 (69)
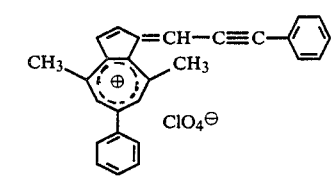 (70)
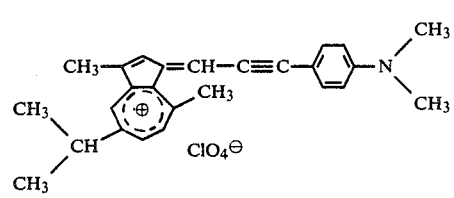 (71)
Compounds represented by the general formula (11):
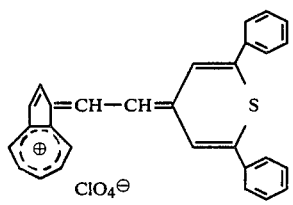 (72)
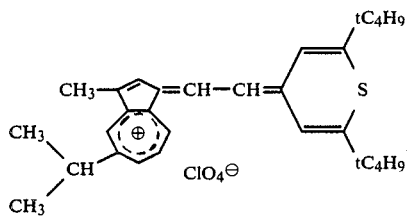 (73)
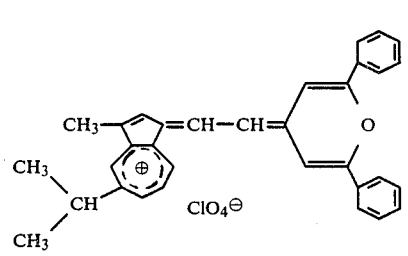 (74)

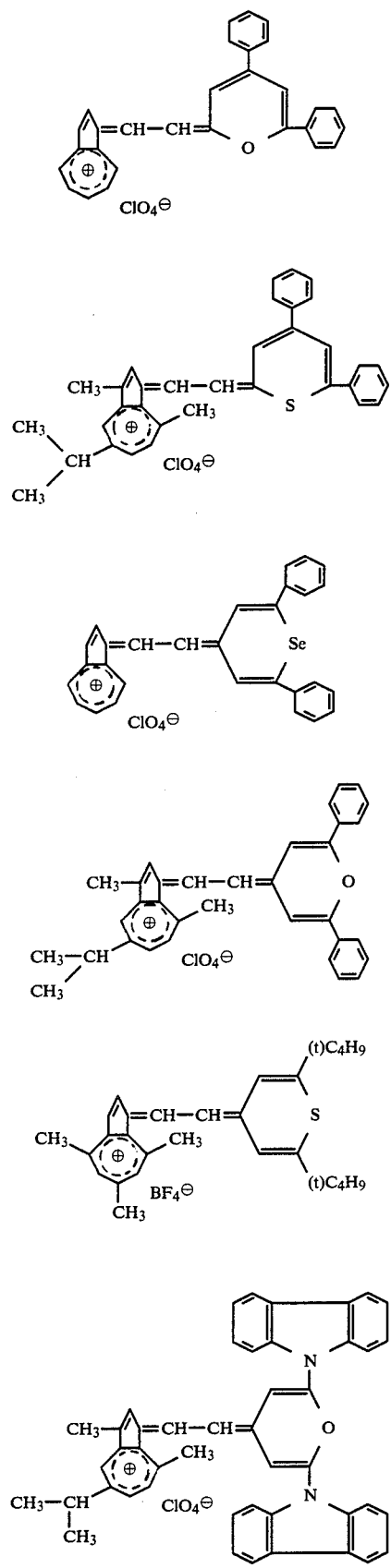
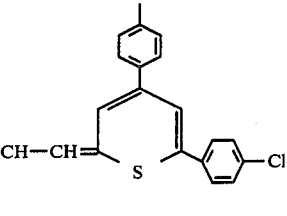
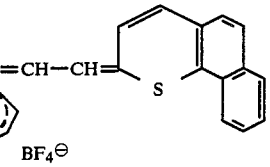
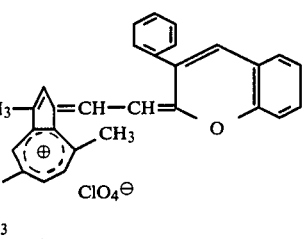
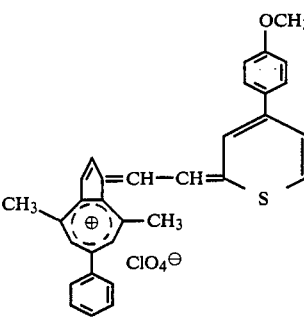
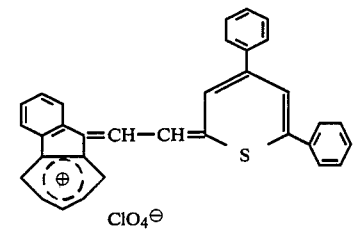

Compounds represented by the general formula (1) or (2) can be readily prepared by reacting azulene compounds with squaric acid or croconic acid in a suitable solvent as described in Angew. Chem. Vol. 78, No. 20, p. 937 (1966).

Compounds represented by the general formula (3) wherein n is 0 can be prepared by (1) heating azulene compounds with a 1-formyl-azulene compound, which is described in J. Chem. Soc., 1960, p. 501, in a suitable solvent in the presence of a strong acid, (2) mixing azulene compounds with a 1-ethoxymethyleneazulenium salt in a suitable solvent as described in J. Chem. Soc., 1961, pp. 1724–1730, or (3) heating azulene compounds with 2-hydroxymethylene cyclohexanone in a suitable solvent in the presence of a strong acid as described in J. Chem. Soc., 1961, p. 359.

Compounds represented by the general formula (3) wherein n is 1 or 2 can be prepared by mixing azulene compounds with a malondialdehyde or glutacondialdehyde is a suitable solvent in the presence of a strong acid as described in J. Chem. Soc., 1961, pp. 3591-3592.

Compounds represented by the general formula (4) can be readily prepared by heating azulene compounds with glyoxal in a suitable solvent in the presence of a strong acid as described in J. Chem. Soc., 1961, p. 3588.

Compounds represented by the general formula (5) can be prepared by heating azulene compounds with a 1,3-diformylazulene compound in a suitable solvent in the presence of a strong acid as described in J. Chem. Soc., 1960, p. 501.

Compounds represented by the general formula (6) can be prepared by heating 1-formylazulene compounds with a quaternary ammonium salt of heterocyclic compound having an active methyl group in a suitable solvent as described in J. Chem. Soc., 1961, pp. 163-167.

Compounds represented by the general formula (7), (8), (9), or (10) can be prepared by mixing azulene compounds with the corresponding aldehyde compound in a suitable solvent in the presence of a strong acid as described in J. Chem. Soc., 1958, pp. 1110-1117, ibid., 1960, pp. 494-501, and ibid., 1961, pp. 3579-3593.

Compounds represented by the general formula (11) can be prepared by reacting 1-formylazulene compounds with a compound represented by the general formula (12)

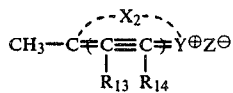
(12)

wherein $X_2$, Y, $R_{13}$, $R_{14}$, $Z^\ominus$, and l are the same as in the general formula (11), in a suitable solvent.

Suitable solvents for the above preparations of compounds of the formulae (1)-(11) are alcohols such as ethanol, butanol, and benzyl alcohol; nitriles such as acetonitrile and propionitrile; organic carboxylic acids such as formic acid, acetic acid, and propionic acid; acid anhydrides such as acetic anhydride; and alicyclic ethers such as dioxane and tetrahydrofuran. Mixed solvents of alcohols such as butanol and benzyl alcohol with aromatic hydrocarbons such as benzene can also be used. The reaction temperature can be selected from the range from room temperature to the boiling point of solvent used, but is generally 80°-120° C., preferably 100°-110° C. The reaction period is generally 10 minutes to 1 hour, preferably 20 to 30 minutes.

Referring to typical examples of the above compounds used in this invention, preparation procedures are illustrated below.

PREPARATION EXAMPLE 1 (COMPOUND NO. 3)

In 80 ml of n-butanol 1.2 g (0.0105 mole) of 3,4-dihydroxy-3-cylobutene-1,2-dione was dissolved by heating with stirring to 100° C. in a 200 ml 3-necked flask.

Then, 3 ml of quinoline, 4.46 g (0.0225 mole) of 1,4-dimethyl-7-isopropylazulene, and 30 ml of benzene were added successively to the solution to start reaction. The reaction was continued for 5 hours at 95°-110° C. while adding in parts 45 ml of benzene and 30 ml of n-butanol and removing water by azeotropic distillation therewith.

The reaction mixture was cooled and filtered with suction. The filter cake was washed with 50 ml of n-butanol and then with 100 ml of methanol, giving a crude pigment. Twice boiling-filtration thereof with 100 ml each of tetrahydrofuran gave 3.7 g of the compound No. 3, yield 74.7%, m. p. 237°-239° C. (capillary method).

Anal. Calcd. (%) for $C_{34}H_{34}O_2$: C 86.02, H 7.23. Found (%): C 85.91, H 7.34.

Absorption spectrum in chloroform: $\lambda$ max=770 nm

PREPARATION EXAMPLE 2 (COMPOUND NO. 12)

A mixture of 1.25 ml of 70% perchloric acid and 7.5 ml of ethanol was added to a solution of 0.64 g of azulene in a mixture of 7.5 ml of ethyl orthoformate and 15 ml of ethanol at room temperature while stirring. Black needle-like crystals were soon oberved to separate out. The mixture, stirred at room temperature for 40 minutes, was filtered with suction to give a crude precipitate of the compound No. 12. It was twice rinsed and filtered with 20 ml each of ethanol, suspended in 30 ml of water, and filtered after a 30-minute stirring. The filter cake was washed again with 20 ml of ethanol and dried giving 0.87 g of the compound No. 12, yield 95%, m. p. 260° C. or higher (capillary method).

Absorption spectrum in dichloromethane: $\lambda$ max=623 nm

Anal. Calcd. (%) for $C_{21}H_{15}ClO$: C 68.76, H 4.13, Cl 9.66. Found (%): C 68.61, H 4.03, Cl 9.34.

PREPARATION EXAMPLE 3 (COMPOUND NO. 13)

A mixture of 1.0 g of azulene, 2.77 g of 3-ethoxymethyleneguaiazulenium perchlorate, and 47 ml of methanol was refluxed with stirring for 5 minutes and allowed to stand overnight. The formed precipitate was filtered off, washed with 20 ml of methanol, and dried giving 2.35 g of a crude product (crude yield: 69%). Recrystallization of 2.0 g of the crude product from acetonitrile gave 1.3 g of the compound No. 13, m. p. 194°-196° C. (capillary method).

Absorption spectrum in methylene chloride: $\lambda$ max=648 nm

Anal. Calcd. (%) for $C_{26}H_{25}ClO_4$: C 71.46, H 5.78, Cl 8.11. Found (%): C 71.24, H 5.81, Cl 8.17.

PREPARATION EXAMPLE 4 (COMPOUND NO. 21)

A mixture of 2.4 g of 1,4-dimethyl-7-isopropylazulene, 3.0 g of 40% aqueous glyoxal solution, 50 ml of acetonitrile, and 3.0 ml of 70% perchloric acid was heated with stirring at 75°-80° C. for 4 minutes and left cooling. The next day, the formed precipitate was filtered off, rinsed with 15 ml of acetonitrile, and dried after filtration, giving 1.53 g of the compound No. 21, yield 40.8%, m. p. 260° C. or higher (capillary method).

Absorption spectrum in acetonitrile: $\lambda$ max=534 nm

Anal. Calcd. (%) for $C_{32}H_{36}Cl_2O_8$: C62.03, H 5.87, Cl 11.44. Found (%): C 61.97, H 5.96, Cl 11.78.

PREPARATION EXAMPLE 5 (COMPOUND NO. 26)

A mixture of 1.4 g of 1,3-diformylazulene, 3.0 g of 1,4-dimethyl-7-isopropylazulene, and 70 ml of glacial acetic acid was heated with stirring to 105° C.

After addition of 3.4 ml of 70% perchloric acid, the mixture was kept at the same temperature for 5 minutes and allowed to stand overnight. The formed precipitate was filtered off, rinsed and filtered once with 10 ml of glacial acetic acid and then twice with 50 ml each of water, and dried giving 2.4 g of a crude product (yield 65%). Recrystallization of 2.0 g of the crude product from acetonitrile gave 1.2 g of the compound No. 26, m. p. 260° C. or higher (capillary method).

Absorption spectrum in glacial acetic acid: $\lambda$ max=660 nm

Anal. Calcd. (%) for $C_{42}H_{42}Cl_2O_8$: C 67.64, H 5.69, Cl 9.51. Found (%): C 67.76, H 5.78, Cl 9.31.

PREPARATION EXAMPLE 6 (COMPOUND NO. 34)

A mixture of 0.60 g of 1-formyl-5-isopropyl-3,8-dimethylazulene, 0.79 g of 4-methyl-1-ethylquinolinium iodide, 1.8 ml of piperidine, and 22 ml of ethanol was heated with stirring to react at 75°-80° C. for 10 minutes and was allowed to stand overnight. Crystals separated out were filtered off, rinsed and filtered twice with 10 ml each of ethanol, and dried giving 0.72 g of the compound No. 34, yield 55%, m. p. 243°-245° C. (capillary method).

Absorption spectrum in dichloromethane: $\lambda$ max=644 nm

Anal. Calcd. (%) for $C_{28}H_{20}IN$: C 66.26, H 5.97, N 2,76, I 25.01. Found (%): C 66.34, H 5.81, N 2.71 I 25.14.

PREPARATION EXAMPLE 7 (COMPOUND NO. 39)

A solution of 7.92 g of 1,4-dimethyl-7-isopropylazulene in 400 ml of tetrahydrofuran was added dropwise to a solution of 5.96 g of p-dimethylaminobenzaldehyde and 10 ml of 70% perchloric acid in 400 ml of tetrahydrofuran at room temperature. The mixture, stirred for 2 hours, was allowed to stand overnight. The formed precipitate was filtered off, rinsed and filtered three times with 100 ml each of tetrahydrofuran, then twice with 200 ml each of water, and further once with 100 ml of tetrahydrofuran, and dried giving 10.40 g of the compound No. 39, yield 60.6%, m. p. 160.5°-162° C. (capillary method).

Absorption spectrum in acetone: $\lambda$ max=640 nm

Anal. Calcd. (%) for $C_{24}H_{28}ClNO_4$: C 67.04, H 6.58, N 3.26, Cl 8.25. Found (%): C 67.17, H 6.68, N 3.19, Cl 8.16.

PREPARATION EXAMPLE 8 (COMPOUND NO. 50)

A solution of 1.28 g of azulene in 150 ml of acetic acid was added dropwise to a solution of 1.50 g of p-dimethylaminobenzaldehyde and 5.0 ml of 70% perchloric acid in 150 ml of acetic acid at room temperature. After one-hour stirring of the mixture, the resulting precipitate was filtered off, washed with 100 ml of acetic acid, suspended in 250 ml of water, and filtered again after a 30-minute stirring. After 7 times of rinse and filtration with 200 ml each of water, the precipitate was dried giving 2.41 g of the compound No. 50, yield 67.0%, m. p. 260° C. or higher (capillary method).

Absorption spectrum in acetonitrile: $\lambda$ max=634 nm

Anal. Calcd. (%) for $C_{19}H_{18}ClNO_4$: C 63.42, H 5.05, N 3.89, Cl 9.85. Found (%): C 64.58, H 5.32, N 4.04, Cl 9.64.

PREPARATION EXAMPLE 9 (COMPOUND NO. 54)

After 2.26 g of N-ethyl-3-formylcarbazole and 2.0 g of guaiazulene (G 11004 of Aldrich Chemical Co.) were dissolved in 160 ml of tetrahydrofuran, and 5.0 ml of 70% perchloric acid was added to the solution at room temperature, were reacted at 60°-65° C. for 10 minutes. The resulting mixture was cooled and allowed to stand for 24 hours. The formed precipitate was filtered off, and after four times of rinse and filtration with 40 ml each of tetrahydrofuran, was dried giving 3.37 g of a crude product (yield 66.2%). Recrystallization of 0.9 g of the crude product from a methyl ethyl ketone-acetonitrile (8:5) mixture gave 0.42 g of the compound No. 54, m. p. 206°-208° C. (capillary method).

Absorption spectrum in dichloromethane: $\lambda$ max=612 nm

Anal. Calcd. (%) for $C_{30}H_{30}ClNO_4$: C 71.48, H 6.01, N 2.78, Cl 7.03. Found (%): C 72.04, H 6.14, N 2.80, Cl 7.01.

An infrared absorption spectrum of this product is shown in FIG. 1.

PREPARATION EXAMPLE 10 (COMPOUND NO. 63)

A solution of 1.77 g of p-dimethylaminocinnamic aldehyde and 2.0 g of guaiazulene (G 1100-4 of Aldrich Chemical Co.) in 50 ml of acetic acid was heated to 103° C. The reaction was conducted at 103°-106° C. for 20 minutes by adding 2.0 g of 70% perchloric acid. The product mixture was cooled and allowed to stand for 24 hours. The formed precipitate was filtered off, and its rinse and filtration were repeated three times with 50 ml each of acetic acid, twice with 250 ml each of water, and further twice with 250 ml each of ethanol. The filter cake on drying gave 1.88 g of the compound No. 63, yield 40.9%.

Absorption spectrum in dichloromethane: $\lambda$ max=728 nm

Anal. Calcd. (%) for $C_{26}H_{30}ClNO_4$: C 68.48, H 6.64, N 3.07, Cl 7.77. Found (%): C 68.57, H 6.73, N 3.14, Cl 7.64.

Figure 2:
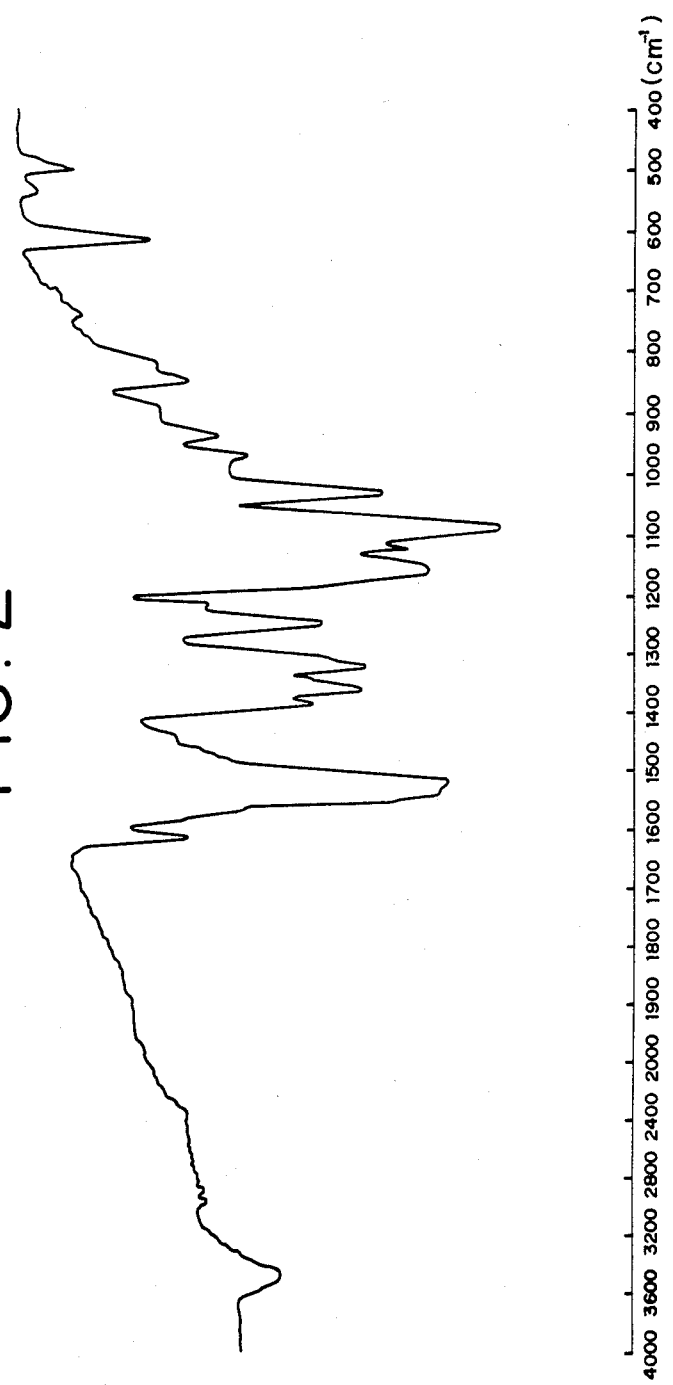
FIG. 2 illustrates that of the compound No. 63.

An infrared spectrum of this product is shown in FIG. 2.

PREPARATION EXAMPLE 11 (COMPOUND NO. 68)

A solution of 2.0 g of phenylpropargylaldehyde (P 3100-0 mfd. by Aldrich Chemical Co.) in 20 ml of acetonitrile was added dropwise to a mixture of 3.0 g of guaiazulene, 2.5 ml of 70% perchloric acid, and 40 ml of acetonitrile at room temperature. After 2-hour stirring, the formed precipitate was filtered off, twice rinsed with 20 ml each of acetonitrile, and dried giving 3.73 g of the compound No. 68, yield 60.0%, m. p. 199°-200° C. (capillary method).

Absorption spectrum in methylene chloride: $\lambda$ max=501 nm

Anal. Calcd. (%) for $C_{24}H_{23}ClO_4$: C 70.15, H 5.65, Cl 8.63. Found (%): C 70.06, H 5.74, Cl 8.68.

PREPARATION EXAMPLE 12 (COMPOUND NO. 76)

In 100 ml of glacial acetic acid 3.0 g of 1-formyl-3,8-dimethyl-5-isopropylazulene and 4.8 g of 2-methyl-4,6-diphenylthiopyrylium perchlorate were reacted at 90°-105° C. for 40 minutes. After cooling of the product mixture, separated crystals were filtered off, washed with 50 ml of glacial acid, then with 500 ml of water, and further twice with 250 ml each of ethanol, and dried giving 7.0 g of the compound No. 78, yield 93%, decomp. point 240°–242° C.

Absorption spectrum in dichloromethane: $\lambda$ max = 743 nm

Anal. Calcd. (%) for $C_{34}H_{31}ClO_4S$: C 71.49, H 5.48, Cl 6.21. Found (%): C 71.36, H 5.54, Cl 6.29.

PREPARATION EXAMPLE 13 (COMPOUND NO. 78)

In 100 ml of acetic anhydride 3.0 g of 1-formyl-3,8-dimethyl-5-isopropylazulene and 4.6 g of 4-methyl-2,6-diphenylpyrylium perchlorate were reacted at 80°–90° C. for 20 minutes. After cooling, separated crystals were filtered off, washed with 50 ml of glacial acetic acid, then with 600 ml of water, and further twice with 250 ml each of ethanol, and dried giving 6.7 g of the compound No. 78, yield 91%.

Absorption spectrum in dichloromethane: $\lambda$ max = 686 nm

Anal. Calcd. (%) for $C_{34}H_{31}ClO_5$: C 73.56, H 5.64, Cl 6.39. Found (%): C 73.43, H 5.80, Cl 6.45.

Films comprising the above azulenium compounds exhibit photoconductivity and accordingly can be used for the following photoconductive layers of electrophotographic photosensitive members.

In this invention, electrophotographic photosensitive members can be prepared by vacuum deposition of the above azulenium compounds or application of a dispersion thereof in a suitable binder, on electrically conductive substrates.

In preferred embodiments of this invention, the above photoconductive films can be applied as the charge generation layer of an electrophotographic photosensitive member having two photosensitive layers which function as a charge generation layer and as a charge transport layer, respectively.

The charge generation layer is desired to contain the above photoconductive compound as much as possible for the purpose of absorbing most of the incident light to generate a great number of charge carriers. Additionally, the charge generation layer is desirably as thin as $5\mu$ or less, preferably $0.01-1\mu$, for the purpose of effective injection of the generated charge carriers into the charge transport layer without substantial deactivation of the carriers due to the recombination or capture (trapping).

The charge generation layer can be formed, as stated above, by applying a dispersion of the above azulenium compound in a suitable binder on a substrate or by vacuum deposition of the compound on a substrate using a vacuum deposition apparatus. Suitable binders can be selected from a wide variety of insulating resins and from organic photoconductive polymers such as poly(N-vinylcarbazole), polyvinylanthracene, polyvinylpyrene, and the like. Preferred examples of the binder are insulating resins such as poly(vinyl butyral), polyarylates (including a condensation polymer of bisphenol A and phthalic acid), polycarbonates, polyesters, phenoxy resins, poly(vinyl acetate), acrylic resins, polyacrylamides, polyamides, polyvinylpyridine, cellulosic resins, urethane resins, epoxy resins, casein, poly(vinyl alcohol), and polyvinylpyrrolidone. Contents of the binder resin in the charge generation layer are up to 80%, preferably up to 40%, by weight.

Solvents suitable for these resins vary depending upon the kind of resin and it is desirable to select those not dissolving the charge transport layer or undercoating layer, which will be described later in detail. As examples of the solvents, there may be cited alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate and ethyl acetate; halogenated aliphatic hydrocarbons such as chloroform, methylene chloride, dichloroethylene, carbon tetrachloride, and trichloroethylene; and aromatic hydrocarbons or halogenated aromatic hydrocarbons such as benzene, toluene, xylene, ligroin, monochlorobenzene, and dichlorobenzene.

The coating can be accomplished by dip coating, spray coating, spinner coating, bead coating, Meyer bar coating, blade coating, roller coating, curtain coating, and the like. The coating film is dried preferably by heating after the set to touch at room temperature. The heat drying can be performed at 30°–200° C. for 5 minutes–2 hours with or without blowing air.

The charge transport layer, being electrically in communication with the charge generation layer, has a function of receiving charge carriers from the charge generation layer in an electric field and a function of transporting these charge carriers to its surface. The charge transport layer may be laminated either on the upper side or the lower side (substrate side) of the charge generation layer, but preferably on the upper side.

A material transporting charge carrier in the charge transport layer (hereinafter, simply referred to as "charge-transporting material") is desirably substantially insensitive to electromagnetic waves to which the charge generation layer is sensitive. The electromagnetic waves herein referred to mean rays of light in a broad sense including $\gamma$-rays, X-rays, ultraviolet rays, visible rays, near-infrared rays, infrared rays, far infrared rays, etc. When the wavelength region of rays to which the charge transport layer is sensitive agrees or overlaps with that of rays to which the charge generation layer is sensitive, the charge carriers generated in both layers tend to attack each other, thus the sensitivity lowered.

The charge-transporting materials are classified into electron-transporting materials and hole-transporting materials. Electron-transporting materials utilizable in this invention include electron attractive materials, e.g. chloranyl, bromanyl, tetracyanoethylene, tetracyanoquinodimethane, 2,4,7-trinitro-9-fluorenone, 2,4,5,7-tetranitro-9-fluorenone, 2,4,7-trinitro-9-dicyanomethylenefluorenone, 2,4,5,7-tetranitroxanthone, and 2,4,8-trinitrothioxanthone, and their polymeric materials.

Hole-transporting materials utilizable include pyrene, N-ethylcarbazole, N-isopropylcarbazole, N-methyl-N-phenylhydrazino-3-methylidene-9-ethylcarbazole, N,N-diphenylhydrazino-3-methylidene-9-ethylcarbazole, N,N-diphenylhydrazino-3-methylidene-10-ethylphenothiazine, N,N-diphenylhydrazino-3-methylidene-10-ethylphenoxazine; hydrazones such as p-diethylaminobenzaldehyde-N,N-diphenylhydrazone, p-diethylaminobenzaldehyde-N-$\alpha$-naphthyl-N-phenylhydrazone, pyrrolidinylbenzaldehyde-N,N-diphenylhydrazone, 1,3,3-trimethylindolenine-ω-aldehyde-N,N-diphenylhydrazone, and p-diethylaminobenzaldehyde-3-methylbenzthiazolinone-2-hydrazone; 2,5-bis(p-diethylaminophenyl)-1,3,4-oxadiazole; pyrazolines such as 1-phenyl-3-(p-diethylaminostyryl)-5-(p-diethylaminophenyl)pyrazoline, 1-[quinolyl(2)]-3-(p-diethylaminostyryl)-5-(p-diethylaminophenyl)pyrazoline, 1-[pyridyl(2)]-3-(p-diethylaminostyryl)-5-(p-diethylaminophenyl)pyrazoline, 1-[6-methoxypyridyl(2)]-3-(p-diethylaminostyryl)-5-(p-diethylaminophenyl)-pyrazoline, 1-[pyridyl(3)]-3-(p-diethylaminostyryl)-5-(p-diethylaminophenyl)pyrazoline, 1-[lepidyl(2)]-3-(p-diethylaminostyryl)-5-(p-diethylaminophenyl)pyrazoline, 1-[pyridyl(2)]-3-(p-diethylaminostyryl)-4-methyl-5-(p-diethylaminophenyl)pyrazoline, 1-[pyridyl(2)]-3-(α-methyl-p-diethylaminostyryl)-5-(p-diethylaminophenyl)pyrazoline, 1-phenyl-3-(p-diethylaminostyryl)-4-methyl-5-(p-diethylaminophenyl)pyrazoline, 1-phenyl-3-(α-benzyl-p-diethylaminostyryl)-5-(p-diethylaminophenyl)pyrazoline, and spiropyrazoline; oxazole compounds such as 2-(p-diethylaminostyryl)-6-diethylaminobenzoxazole and 2-(p-diethylaminophenyl)-4-(p-dimethylaminophenyl)-5-(2-chlorophenyl)oxazole; thiazole compounds such as 2-(p-diethylaminostyryl)-6-diethylaminobenzothiazole; triarylmethane compounds such as bis(4-diethylamino-2-methylphenyl)-phenylmethane polyarylalkanes such as 1,1-bis(4-N,N-diethylamino-2-methylphenyl)heptane and 1,1,2,2-tetrakis(4-N,N-dimethylamino-2-methylphenyl)ethane; triphenylamine, poly(N-vinylcarbazole), polyvinylpyrene, polyvinylanthracene, polyvinylacridine, poly(9-vinylphenylanthracene), pyrene-formaldehyde resin, and ethylcarbazole-formaldehyde resin.

Besides these organic charge-transporting materials, such inorganic materials as selenium, selenium-tellurium, amorphous silicon, and cadmium sulfide can also be used.

These charge-transporting materials can be used singly or in combination of two or more.

When the charge-transporting material employed has no film-forming ability, its coating film can be formed by mixing with a suitable binder. Such binders are insulating resins including, for example, acrylic resins, polyarylates, polyesters, polycarbonates, polystyrene, acrylonitrile-styrene copolymer, acrylonitrile-butadiene copolymer, poly(vinyl butyral), poly(vinyl formal), polysulfone, polyacrylamides, polyamides, and chlorinated rubber; and organic photoconductive polymers including, for example, poly(N-vinylcarbazole), polyvinylanthracene, and polyvinylpyrene.

The charge transport layer cannot be made thicker than necessary because the possible charge-carrier transport distance is limited. Its thickness ranges generally from 5 to 30μ, preferably from 8 to 20μ. For forming the charge transport layer by coating, coating methods as cited above can be applied.

The photosensitive layer having a laminate structure comprising such charge generation and charge transport layers as stated above is formed on a substrate having a conductive layer. The substrates having a conductive layer include: sheets or films having conductivity in themselves, such as aluminium, aluminum alloys, copper, zinc, stainless steel, vanadium, molybdenum, chrominium, titanium, nickel, indium, gold, and platinum; those of plastics (e.g. polyethylene, polypropylene, poly(vinyl chloride), poly(ethylene terephthalate), acrylic resins, polyfluoroethylene) covered with a film formed by vacuum deposition of aluminum, aluminum alloy, indium oxide, tin oxide, indium oxide-tin oxide alloy, or the like; those of plastics coated with a dispersion of conductive particles (e.g. carbon black or silver particles) in a suitable binder; those of plastics and paper impregnated with conductive particles; and those of conductive polymers.

An undercoating layer having a barrier function and a bonding function can be laid between the conductive layer and the photosensitive layer. The undercoating layer can be formed from casein, poly(vinyl alcohol), nitrocellulose, ethylene-acrylic acid copolymer, polyamides (e.g. nylon 6, nylon 66, nylon 610, nylon copolymer, or alkoxymethylated nylon), polyurethanes, gelatin, aluminum oxide, or the like.

Thickness of the undercoating layer is desirably 0.1–5μ, preferably 0.5–3μ.

When using a photosensitive member comprising a conductive layer, charge generation layer, and charge transport layer laminated in this order, it is necessary to provide positive charge to the surface of the charge transport layer if this layer is formed from an electron-transporting material. On image exposure of the photosensitive member after the positive charging, electrons generated in the charge generation layer, in the exposed area, are injected into the charge transport layer, then arrive at the surface, and neutralize the positive charges, thus decaying the surface potential and producing an electrostatic contrast to the unexposed area. The thus produced electrostatic latent images, on development with a negative-working toner, turn into visible images. The toner images can be fixed directly or after being transferred to a transfer recording medium such as paper or a plastic film.

It is also possible that the electrostatic latent images on the photosensitive member are transferred to the insulating layer of transfer paper, then developed, and fixed. Any of the known developers, development processes, and fixing processes may be adopted, viz. there are no particular restrictions thereupon. These electrophotographic operations can be repeated twice or more.

On the other hand, if the charge transport layer is formed from a hole-transporting material, its surface needs to be negatively charged. On image exposure of the photosensitive member after the negative charging, holes generated in the charge generation layer, in the exposed area, act similarly to the electrons stated above, thus forming electrostatic latent images. For developing the latent images, it is necessary to use a positive-working toner, contrary to the case where an electron-transporting material is used.

For the image exposure, various radiations can be used including those emitted from a halogen lamp, xenon lamp, mercury lamp, and the like as well as short-pulsed rays such as lasers having a wavelength in the visible to infrared region, e.g. a gallium-arsenic-aluminum semiconductor laser (λ=820 nm), argon gas laser (λ=488 nm, 515 nm), and helium-neon gas laser (λ=632.8 nm); and rays from a xenon flash lamp.

In another embodiment of this invention, the azulenium compound described above can be incorporated as a sensitizer into photosensitive films comprising an organic photoconductive material such as the above-cited hole-transporting material, e.g. hydrazones, pyrazolines, oxazoles, thiazoles, triarylmethanes, polyarylalkanes, triphenylamine, poly(N-vinylcarbazoles), or the like or an inorganic photoconductive material such as zinc oxide, cadmium sulfide, selenium, or the like. These photosensitive films are formed by a coating method from mixtures, containing the azulenium compounds, of the above photoconductive material and a binder.

Any photosensitive member of this invention contains at least one azulenium salt selected from the compounds represented by the general formula (I), (II), or (III) and if necessary, can be improved in sensitivity or made panchromatic by incorporating another photoconductive pigment or dye having a different absorption spectrum.

Figure 3:
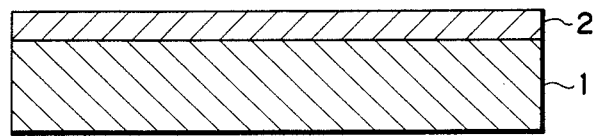
FIGS. 3 and 4 are sectional views of preferred optical recording media of this invention.

In another embodiment of this invention, the above-mentioned radiation-sensitive film can be used as the optical recording layer of an optical recording medium, which has a structure, for instance, as shown in FIG. 3 comprising a substrate 1 and an overlying thin film 2 containing the above-mentioned organic compound. This thin film 2 can be formed from the compound of the general formula (I), (II), or (III) by vacuum deposition or from a coating liquid containing said compound and a binder by coating. In the case of the coating, the above-mentioned organic compound contained in the binder may be either in heterogeneous form or in homogeneous form.

Suitable binders for the coating can be selected from a wide variety of resins including, for example, cellulose esters such as nitrocellulose, cellulose phosphate, cellulose sulfate, cellulose acetate, cellulose propionate, cellulose butyrate, cellulose myristate, cellulose palmitate, cellulose acetate-propionate, and cellulose acetate-butyrate; cellulose ethers such as methyl cellulose, ethyl cellulose, propyl cellulose, and butyl cellulose; vinyl type resins such as polystyrene, poly(vinyl chloride), poly(vinyl acetate), poly(vinyl butyral), poly(vinyl acetal), poly(vinyl alcohol), and polyvinylpyrrolidone; copolymer resins such as styrene-butadiene copolymer, styrene-acrylonitrile copolymer, styrene-butadiene-acrylonitrile copolymer, and vinyl chloride-vinyl acetate copolymer; acrylic resins such as poly(methyl methacrylate), poly(methyl acrylate), poly(butyl acrylate), poly(acrylic acid), poly(methacrylic acid), polyacrylamide, and polyacrylonitrile; polyester resins such as poly(ethylene terephthalate); polyarylate resins such as poly(4,4'-isopropylidenediphenylene-co-1,4-cyclohexylenedimethylene carbonate), poly(ethylene-dioxy-3,3'-phenylene thiocarbonate), poly(4,4'-isopropylidenediphenylene carbonate-coterephthalate), poly(4,4'-isopropylidenediphenylene carbonate), poly(4,4'-sec-butylidenediphenylene carbonate), and poly(4,4'-isopropylidenediphenylene carbonate-block-oxyethylene); polyamides; polyimides; epoxy resins; phenolic resins; and polyolefins such as polyethylene, polypropylene, and chlorinated polyethylene.

Organic solvents suitable for the coating depend upon the kind of the binder and whether the above-mentioned compound is intended to be in heterogeneous form or homogenious form in the binder, but the following solvents can be generally used: alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate, ethyl acetate, and butyl acetate; halogenated aliphatic hydrocarbons such as chloroform, methylene chloride, dichloroethylene, carbon tetrachloride, and trichloroethylene; and aromatic hydrocarbons or chlorinated derivatives thereof, such as benzene, toluene, xylene, ligroin, monochlorobenzene, and dichlorobenzene.

The coating can be carried out by dip coating, spray coating, spinner coating, bead coating, Meyer bar coating, blade coating, roller coating, curtain coating and the like.

When forming the film 2 (in FIG. 3) together with a binder, the above-mentioned organic compound may be contained in the film in amounts of generally 1–90%, preferably 20–70%, by weight. Thickness of the film 2, dry coating film or vacuum deposition film, is generally up to $10\mu$, preferably up to $2\mu$.

Materials suitable for the substrate 1 include: plastics such as polyesters, acrylic resins, polyolefin resins, phenolic resins, epoxy resins, polyamides, and polyimides; glass; and metals.

Figure 4:
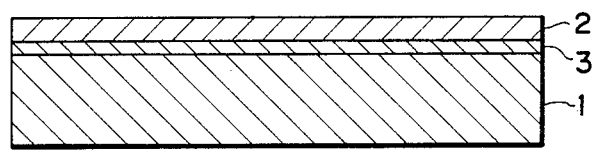

The optical recording medium of this invention, comprising the thin film 2 (electromagnetic-radiation-sensitive layer) and its substrate 1, can be provided with various kinds of auxiliary layer. For example, the substrate 1 can be overlaid with an inorganic or organic film for the purpose of adjusting thermal properties. The radiation-sensitive layer 2 can be covered with a protective coating layer of a clear material. This protective coating layer is effective in not only preventing the mechanical damage of the thin film 2 but also improving the sensitivity because the reflection of incident light can be reasonably inhibited with the coat of a proper thickness. Further, as shown in FIG. 4, a reflection layer 3 can be provided between the electromagnetic radiation-sensitive layer 2 and the substrate 1. This reflection layer 3 can be formed by vacuum deposition of a highly reflective metal such as aluminum, silver, or chromium or by laminating a foil of such a metal, on the substrate 1.

The optical recording medium of this invention can be provided previously on its surface with pregrooves which function as guiding or addressing grooves.

Figure 5:
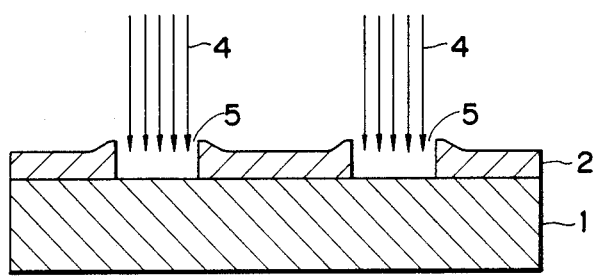
FIG. 5 is an illustration of an embodiment making a record in an optical recording medium according to this invention.
Figure 6:
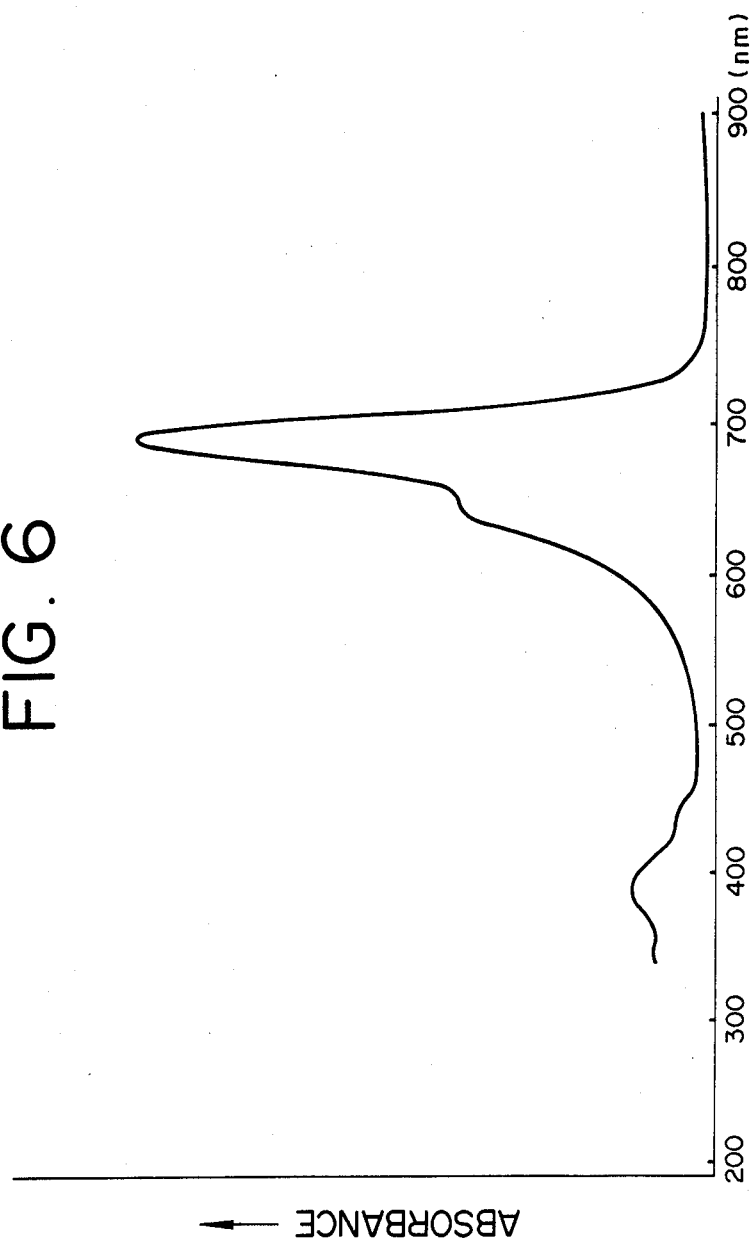

In the optical recording medium of this invention, as shown in FIG. 5, pits 5 are formed in the thin film 2 by irradiating it with electromagnetic radiation 4 or contacting it with a heater. Radiation sources suitable for this purpose include: lasers having a wavelength in the visible to infrared region, e.g. a gallium-arsenic-aluminum semiconductor laser ($\lambda=820$ nm), argon gas laser ($\lambda=488$ nm, 515 nm), and helium-neon gas laser ($\lambda=632.8$ nm); other short pulsed rays from various lamps such as a xenon flash lamp; and an infrared lamp. The pits differ in reflectance from the pit-free area. Hence, pits can be formed on the optical recording medium by scanning it with pulses of an electromagnetic radiation along a track, and the difference of reflectance can be read by means of a photodetector by scanning the recording medium with a low output laser along with the track.

Advantageous effects of the thin film according to this invention are as follows: The electromagnetic-radiation-sensitive layer exhibits high efficiencies of absorbing electromagnetic radiations, in particular long wavelength lasers. Electrophotographic photosensitive members and optical recording media provided with this coating film permit image formation or recording thereupon by use of a semiconductor laser having a long wavelength as well as a low energy density helium-neon gas laser and rays from a xenon flash lamp. These optical recording media exhibit a high S/N ratio and a good reproduction efficiency.

This invention is illustrated in more detail referring to the following Examples:

EXAMPLES 1 to 25

A solution of casein in aqueous ammonia (casein 11.2 g, 28% aq. ammonia 1 g, water 222 ml) was applied to aluminum sheets by means of a Meyer bar and dried to form an intermediate layer $0.1\mu$ thick on each sheet.

25 kinds of coating liquids were prepared by adding 5 g each of 25 kinds of azulenium salts shown in the following table to a solution of 2 g of a vinyl butyral resin (degree of butyral conversion 63 mole %) in 95 ml of isopropanol.

After dispersing in an attritor, the coating liquids were applied separately onto the casein intermediate layers by means of a Meyer bar and dried to form charge generation layers each $0.1\mu$ thick.

A solution was prepared by dissolving 5 g of a hydrazone compound represented the formula

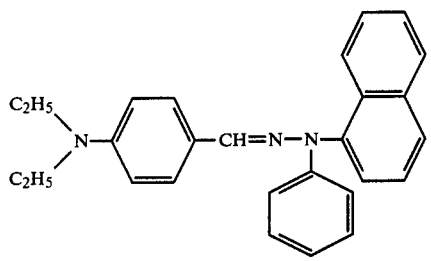

and 5 g of a poly(methyl methacrylate) resin (number average mol. wt. 100,000) in 70 ml of benzene. The solution was applied to the charge generation layers by means of a Meyer bar and dried to form charge transport layers each $12\mu$ thick.

The thus prepared 25 kinds of electrophotographic photosensitive members were corona-charged at $-5$ KV in the static fashion by using an electrostatic copying paper testing machine (Model SP-428, mfd. by Kawaguchi Denki, Co., Ltd.), were retained for 10 seconds in the dark, and exposed to light at an intensity of 5 lux to examine their light discharging properties. The results are shown in Table 1, wherein Vo is the original potential of the charged surface, Vk is the potential retention (%) after its decaying for 10 seconds in the dark, and $E\frac{1}{2}$ is the exposure quantity for halving the potential after decaying for 10 seconds in the dark.

TABLE 1

| Example No. | Azulenium salt (compound No.) | Vo (−V) | Vk (%) | E ½ (lux · sec) |
|---|---|---|---|---|
| 1 | 1 | 570 | 89 | 4.5 |
| 2 | 2 | 620 | 87 | 10.4 |
| 3 | 3 | 590 | 90 | 11.6 |
| 4 | 4 | 580 | 88 | 9.2 |
| 5 | 9 | 560 | 85 | 18.7 |
| 6 | 10 | 570 | 89 | 10.5 |
| 7 | 12 | 600 | 85 | 7.4 |
| 8 | 13 | 570 | 88 | 16.8 |
| 9 | 15 | 580 | 86 | 17.9 |
| 10 | 17 | 590 | 90 | 14.6 |
| 11 | 21 | 600 | 84 | 35.2 |
| 12 | 26 | 580 | 89 | 21.0 |
| 13 | 34 | 590 | 91 | 7.8 |
| 14 | 39 | 570 | 86 | 4.3 |
| 15 | 40 | 580 | 89 | 25.0 |
| 16 | 41 | 560 | 84 | 17.5 |
| 17 | 42 | 590 | 89 | 21.0 |
| 18 | 45 | 570 | 88 | 13.8 |
| 19 | 49 | 600 | 86 | 11.3 |
| 20 | 50 | 580 | 89 | 7.5 |
| 21 | 54 | 550 | 84 | 18.8 |
| 22 | 60 | 590 | 87 | 13.5 |
| 23 | 61 | 600 | 89 | 18.6 |
| 24 | 63 | 560 | 91 | 2.8 |
| 25 | 68 | 570 | 87 | 31.4 |

Unless otherwise noted, light discharging properties of photosensitive members in the following Examples were measured as stated above.

EXAMPLE 26

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt No. 1 in the solution. The dispersion was applied to an aluminum layer vapor-deposited on a polyester film and was dried to prepare a photosensitive member having a photosensitive layer $13\mu$ thick.

Light discharging properties of this photosensitive member were as follows:

| | |
|---|---|
| Vo | −480 V |
| Vk | 82% |
| E ½ | 28.7 lux · sec |

EXAMPLES 27–34 AND 87

Photosensitive members were prepared in the same manner as in Example 26 except that azulenium salts shown in the following Table were used in place of the azulenium salt No. 1. Light discharging properties of these photosensitive members are shown in Table 2.

TABLE 2

| Example No. | Azulenium salt (compound No.) | Vo (−V) | Vk (%) | E ½ (lux · sec) |
|---|---|---|---|---|
| 27 | 2 | 500 | 84 | 29.7 |
| 28 | 3 | 510 | 88 | 30.7 |
| 29 | 10 | 470 | 87 | 48.3 |
| 30 | 12 | 500 | 86 | 28.1 |
| 31 | 17 | 480 | 84 | 27.3 |
| 32 | 22 | 510 | 90 | 57.0 |
| 33 | 34 | 460 | 88 | 40.5 |
| 34 | 50 | 510 | 87 | 35.8 |
| 87 | 60 | 500 | 85 | 21.2 |

EXAMPLE 35

A coating dispersion was prepared by adding 1 g of poly(N-vinylcarbazole) and 5 mg of the azulenium salt No. 39 to 10 g of 1,2-dichloroethane, followed by sufficient stirring. The dispersion was applied by doctor blade coating to an aluminum layer vapor-deposited on a poly(ethylene terephthalate) film and was dried to form a photosensitive layer $15\mu$ thick.

Light discharging properties of the photosensitive member thus prepared were as follows (positive charging polarity):

| | |
|---|---|
| Vo | +470 V |
| Vk | 83% |

| | |
|---|---|
| E½ | 29.7 lux · sec |

EXAMPLE 36

A photosensitive member was prepared in the same manner as in Example 35 but using the azulenium salt No. 12 in place of No. 39. Light discharging properties of this photosensitive member were as follows (positive charging polarity):

| | |
|---|---|
| Vo | +460 V |
| Vk | 81% |
| E½ | 35.7 lux · sec |

EXAMPLE 37

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt No. 20 in a ball mill. The dispersion was applied by doctor blade coating on an aluminum layer vapor-deposited on a poly(ethylene terephthalate) film and was dried to prepare a photosensitive member having a photosensitive layer 21μ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt.

EXAMPLE 38

A 1.1-μ poly(vinyl alcohol) coat was formed on an aluminum layer vapor-deposited on a poly(ethylene terephthalate) film.

A dispersion prepared by mixing 1 wt. part of the azulenium salt No. 3, 1 wt. part of a vinyl butyral resin (S-lec BM-2, mfd. by Sekisui Chem. Co., Ltd.), and 30 wt. part of isopropanol in a ball mill for 4 hours was applied onto the poly(vinyl alcohol) coat by means of a Meyer bar and dried to form a charge generation layer 0.1μ thick.

A solution was prepared by dissolving 5 g of a pyrazoline compound represented by the formula

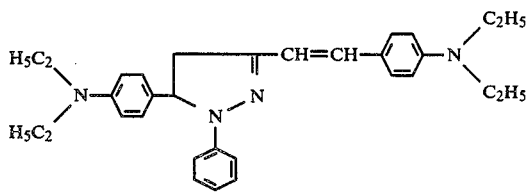

and 5 g of a polyarylate resin (product of polycondensation of bisphenol A with a terephthalic acid-isophthalic acid mixture) in 70 ml of tetrahydrofuran was applied to the charge generation layer and dried to form a charge transport layer 10μ thick.

Light discharging properties of the photosensitive member thus prepared were as follows:

| | |
|---|---|
| Vo | −560 V |
| Vk | 86% |
| E½ | 8.6 lux · sec |

EXAMPLE 39

A solution of casein in aqueous ammonia (casein 11.2 g, 28% aqueous ammonia 1 g, water 222 ml) was applied to an aluminum cylinder by dip coating and dried to form an intermediate layer of 1.0 g/m².

The azulenium salt-containing dispersion prepared in Example 38 was applied to the intermediate layer and dried to form a charge generation layer 0.3μ thick.

A solution was prepared by dissolving 1 wt. part of p-diethylaminobenzaldehyde-N-phenyl-N-α-naphthyl-hydrazone and 1 wt. part of a polysulfone resin (P 1700, mfd. by Union Carbide Corp.) in 6 wt. parts of monochlorobenzene. The solution was applied to the charge generation layer and dried to form a charge transport layer 12μ thick.

Light discharging properties of the photosensitive drum were measured in the same manner as in Example 1 except that a gallium-aluminum-arsenic semiconductor laser (λ780 nm) was used as the light source, the percentage of potential retention, Vk, was measured after 5-second dark decay, and the exposure quantity E½ for halving the potential after 5-second dark decay was expressed in the unit microjoule/cm². The results were as follows:

| | |
|---|---|
| Vo | −520 V |
| Vk | 92% |
| E½ | 2.2 μ joule/cm² |

EXAMPLES 40-52

In the same manner as in Example 39, photosensitive drums were prepared and measured for light discharging properties except that azulenium compounds shown in Table 3 were used in place of the azulenium salt No. 3 for forming the charge generation layers. The results were as shown in Table 3.

TABLE 3

| Example No. | Azulenium salt compound No. | Vo (−V) | Vk (%) | E½ (μjoule/cm²) |
|---|---|---|---|---|
| 40 | 1 | 530 | 89 | 2.1 |
| 41 | 2 | 520 | 86 | 2.5 |
| 42 | 9 | 510 | 87 | 4.4 |
| 43 | 10 | 540 | 85 | 2.0 |
| 44 | 12 | 550 | 82 | 6.5 |
| 45 | 13 | 560 | 84 | 13.2 |
| 46 | 21 | 550 | 83 | 24.6 |
| 47 | 25 | 510 | 86 | 16.9 |
| 48 | 34 | 520 | 88 | 5.7 |
| 49 | 39 | 580 | 86 | 4.9 |
| 50 | 50 | 550 | 82 | 6.4 |
| 51 | 54 | 560 | 84 | 12.0 |
| 52 | 63 | 550 | 85 | 2.3 |

EXAMPLE 53

A solution of casein in aqueous ammonia was applied to an 100-μ aluminum sheet and dried to form a 1.1-μ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt No. 3 were added to a solution of 5 g of a polyester resin (Vylon, mfd. by Toyobo Co., Ltd.) in 70 ml of tetrahydrofuran to form a dispersion, which was applied to the undercoat and dried to form a photosensitive layer 12μ thick.

Light discharging properties of the photosensitive member thus prepared were measured in the same manner as in Example 39 but by positive charging. The results were as follows:

| | |
|---|---|
| Vo | +460 V |
| Vk | 91% |
| E ½ | 5.3 μ joule/cm² |

EXAMPLE 54

A 1.1-μ poly(vinyl alcohol) coat was formed on an aluminum layer vapor-deposited on a poly(ethylene terephthalate) film.

The same dispersion of the azulenium salt No. 3 as used in Example 38 was applied to the poly(vinyl alcohol) coat by means of a Meyer bar and dried to form a charge generation layer 0.5μ thick.

A solution was prepared by dissolving 5 g of a pyrazoline compound represented by the formula

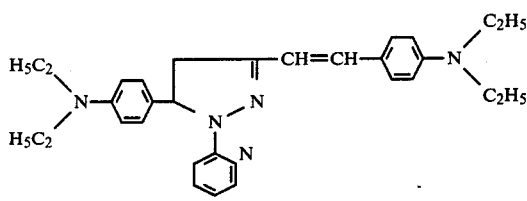

and 5 g of a polyarylate resin (product of polycondensation of bisphenol A with a terephthalic acid-isophthalic acid mixture) in 70 ml of tetrahydrofuran. The solution was applied to the charge generation layer and dried to form a charge transport layer 10μ thick.

Light discharging properties of the photosensitive member thus prepared were measured in the same manner as in Example 39. The results were as follows:

| | |
|---|---|
| Vo | −510 V |
| Vk | 90% |
| E ½ | 3.2 μjoule/cm² |

EXAMPLES 55–65

Photosensitive members were prepared in the same manner as in Examples 1–25 but using 11 kinds of azulenium salts shown in Table 4 for the formation of the charge generation layers. Light discharging properties of these photosensitive member were measured in the same manner as in Example 1. The results are shown in Table 4.

TABLE 4

| Example No. | Azulenium salt (compound No.) | Vo (−V) | Vk (%) | E ½ (lux · sec) |
|---|---|---|---|---|
| 55 | 72 | 520 | 89 | 10.5 |
| 56 | 78 | 580 | 76 | 19.0 |
| 57 | 79 | 535 | 84 | 11.4 |
| 58 | 77 | 540 | 88 | 10.4 |
| 59 | 75 | 600 | 70 | 24.0 |
| 60 | 76 | 500 | 90 | 12.5 |
| 61 | 81 | 540 | 85 | 14.6 |
| 62 | 82 | 570 | 87 | 18.6 |
| 63 | 83 | 490 | 84 | 9.5 |
| 64 | 84 | 510 | 80 | 10.5 |
| 65 | 85 | 480 | 85 | 11.8 |

EXAMPLE 66

A photosensitive member was prepared in the same manner as in Example 26 but using the azulenium salt No. 76 for the formation of the charge generation layer. Light discharging properties of this photosensitive member were as follows:

| | |
|---|---|
| Vo | −510 V |
| Vk | 80% |
| E ½ | 34 lux · sec |

EXAMPLES 67–68

Photosensitive members were prepared in the same manner as in Example 35 but using the azulenium salt Nos. 78 and 80, respectively. Light discharging properties thereof were as follows:

| | Example 67 | Example 68 |
|---|---|---|
| Vo | +490 V | +410 V |
| Vk | 84% | 79% |
| E ½ | 36.8 lux · sec | 32.0 lux · sec |

EXAMPLE 69

A photosensitive member having a photosensitive layer comprising zinc oxide in the same manner as in Example 37 but using the azulenium salt No. 72 in place of No. 20.

Results of measuring the spectral sensitivity of this photosensitive member indicated that the photosensitive layer is sensitive to rays of longer wavelengths as compared with the same zinc oxide layer but not containing such an azulenium salt.

EXAMPLE 70

A coating dispersion was prepared by thoroughly mixing 3 wt. parts of the azulenium compound No. 3, 12 wt. parts of a nitrocellulose solution (OH—less lacquer, mfd. by Daicel Chem. Industries, Ltd., 25 wt. % of nitrocellulose in methyl ethyl ketone), and 70 wt. parts of methyl ethyl ketone. The dispersion was applied by spinner coating to an aluminum layer vapor-deposited on a glass disc of 30 cm in diameter, and was dried to form a recording layer of 0.6 g/m².

The thus prepared optical disc recording medium was placed on a turntable, which was then driven at 1000 rpm with a motor. The rotating disc was spirally recorded by scanning with 8 MHz pulses of a 5-mW output gallium-aluminum-arsenic semiconductor laser (λ=780 nm) converged to a spot size of 1.0μ in diameter.

The recorded surface of the optical disc, on observation with a scanning electron microscope, indicated distinct pits. The track of pits was traced with a low output gallium-aluminum-arsenic semiconductor laser and the reflected beam was detected, giving a sufficiently high S/N ratio.

For the purpose of examining the stability of stored information, the recorded optical disc was allowed to stand for 240 hours under the artificial conditions of 35° C. and 95% R. H., and the surface of the disc was observed also with a scanning electron microscope. As a result, the same distinct pits as before the stability test were recognized. After the test, the track of pits was again traced with the low output gallium-aluminum-arsenic semiconductor laser and the reflected beam was detected, giving a similarly high S/N ratio as before the stability test.

EXAMPLES 71-80

Optical discs were prepared in the same manner using the same materials as in Example 70 except that the azulenium compound No. 3 was replaced by the azulenium compound Nos. 13, 21, 26, 34, 39, 50, 54, 63, 68, and 76, respectively, and the coating weight of the recording layer was changed to 0.8 g/m$^2$ in Examples 73 and 78.

The optical discs thus prepared were subjected to the same information-writing and reading tests and information-storing stability tests as made in Example 70, giving similar good results. That is, in the information writing tests distinct pits were observed on the discs by means of the scanning electron microscope, in the information reading tests the discs exhibited sufficiently high S/N ratios, and the information-storing stability tests proved that the discs maintained the original distinct pits and high S/N ratios.

EXAMPLE 81

A molybdenum boat containing 500 mg of the azulenium compound No. 1 and a glass disc coated with aluminum by vapor deposition were set in a vacuum chamber for vapor deposition use. After the chamber was evacuated to a pressure of $1 \times 10^{-6}$ mmHg or below, the azulenium compound was vapor-deposited to a thickness of 0.2$\mu$ on the aluminum surface while controlling the pressure in the chamber to $1 \times 10^{-5}$ mmHg or below by regulating a heater.

The optical disc recording medium thus prepared was subjected to the same information-writing and reading tests as in Example 70, exhibiting similarly distinct pits and high S/N ratios in the respective tests.

EXAMPLES 82-86

Optical disc recording media were prepared in the same manner as in Example 81 but using the azulenium compound Nos. 4, 8, 12, 27, and 41 in place of No. 1 for the recording layer.

The optical disc recording media were subjected to the same information writing and reading tests as in Example 70, giving good results similar to those in Example 81.

EXAMPLE 88

In the same manner as in Example 39, a photosensitive drum was prepared and measured for light discharging properties except that the azulenium salt No. 4 was used in place of the azulenium salt No. 3 for forming the charge generation layer. The results were as follows:

| | |
|---|---|
| Vo | −530 V |
| Vk V$_5$ (V) | 92% |
| E ½ | 1.8 $\mu$ joule/cm$^2$ |

EXAMPLE 89

A molybdenum boat containing 500 mg of the azulenium compound No. 1 and an aluminum sheet were set in a vacuum chamber for vapor deposition use. After the chamber evacuated to a pressure of $1 \times 10^{-6}$ mmHg or below, the azulenium compound was vapor-deposited on the aluminum sheet to form a charge generation layer 0.2$\mu$ thick while controlling the pressure in the chamber to $1 \times 10^{-5}$ mmHg or below by regulating a heater.

The aluminum sheet overlaid with the charge generation layer was set in another vacuum chamber, which was then evacuated to a pressure of $1 \times 10^{-6}$ mmHg or below. Hydrogen gas and silane gas (15 vol% based on the hydrogen were introduced into the chamber, and a glow discharge was generated by applying a 13.5-MHz high-frequency electric field to form a charge transport layer of amorphous silicon 0.3$\mu$ thick on the charge generation layer.

The photosensitive member thus prepared was set in a charging-exposing test machine, then corona-charged at ⊖5 KV, and irradiated immediately thereafter with a pattern of light which was formed by passing the light of a tungsten lamp through a transmission type of test chart. Immediately thereafter a positive developer (containing a toner and a carrier) was applied to the photosensitive member surface by the cascade technique. Thus, a good toner image was obtained on the photosensitive member surface.

What is claimed is:

1. A radiation-sensitive organic thin film comprising a radiation-sensitive compound having at least one nucleus of an azulenium salt; said compound represented by the following general formula I, II or III:

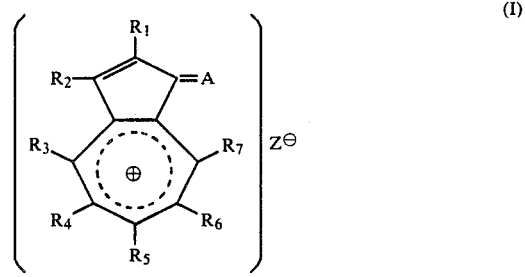

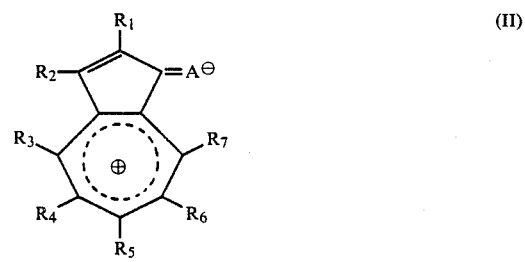

-continued (4)
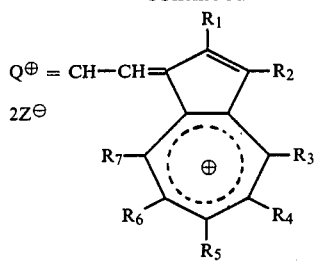

(5)
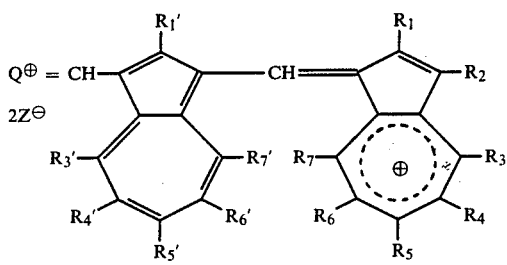

(6)
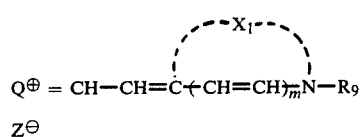

(7)

$Z^{\ominus}$ (8)
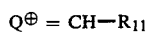

$Z^{\ominus}$ (9)
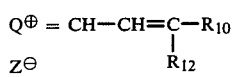

(10)
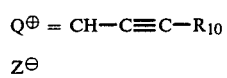

(11)
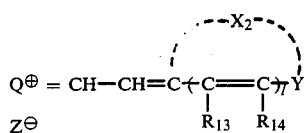

wherein; $Q^{\oplus}$ represents the azulenium residue

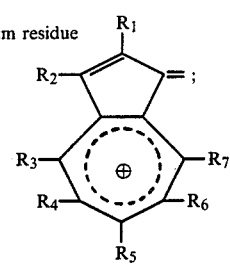

each of $R_1$, $R_2$, $R_3$, $R_4$, $R_5$, $R_6$, and $R_7$ is hydrogen, halogen, or an organic monovalent residue, where at least one of the combinations ($R_1$ and $R_2$), ($R_3$ and $R_4$), ($R_4$ and $R_5$), ($R_5$ and $R_6$), and ($R_6$ and $R_7$) may form a substituted or unsubstituted aromatic ring;

each of $R_1'$, $R_2'$, $R_3'$, $R_4'$, $R_5'$, $R_6'$, and $R_7'$ is hydrogen, halogen, or an organic monovalent residue, where at least one of the combinations ($R_1'$ and $R_2'$), ($R_3'$ and $R_4'$), ($R_4'$ and $R_5'$), ($R_5'$ and $R_6'$), and ($R_6'$ and $R_7'$) may form a substituted or unsubstituted aromatic ring.

$Z^{\ominus}$ is an anionic residue;

$R_8$ is hydrogen, nitro, cyano, alkyl, or aryl;

$R_9$ is substituted or unsubstituted alkyl, substituted or unsubstituted aryl, cycloalkyl, alkenyl, or substituted or unsubstituted aralkyl;

$R_{10}$ is substituted or unsubstituted aryl;

$R_{11}$ is a monovalent heterocyclic residue;

$R_{12}$ is hydrogen, alkyl, or substituted or unsubstituted aryl;

$R_{13}$ and $R_{14}$ each are hydrogen, alkyl, alkoxy, substituted or unsubstituted aryl, substituted or unsubstituted styryl, ring-substituted or unsubstituted 4-phenyl-1,3-butadienyl, or a substituted or unsubstituted heterocyclic residue;

$X_1$ is a nonmetal atomic group necessary to complete a nitrogen-containing heterocyclic residue;

$X_2$ is an atomic group necessary to complete pyrane, thiopyrane, selenopyrane, benzopyrane, benzothiopyrane, benzoselenopyrane, naphthopyrane, naphthothiopyrane, or naphthoselenopyrane ring substituted or unsubstituted;

Y is sulfur, oxygen, or selenium;

n is an integer of 0, 1, or 2; and m is an integer of 0 or 1.

l is an integer of 0 or 1.

25. The optical recording medium of claim 23, which further comprises a substrate and, on the opposite side of said radiation-sensitive organic thin film, a protective layer.

26. The optical recording medium of claim 23, which further comprises a substrate and, on the opposite side of said radiation-sensitive organic thin film, a reflection-preventing layer.

27. The optical recording medium of claim 23, which further comprises a substrate and a reflecting layer provided between said substrate and said radiation-sensitive organic thin film.

28. The optical recording medium of claim 23, wherein said radiation-sensitive organic thin film has a pre-groove.

29. The optical recording medium of claim 28, wherein said pre-groove is a tracking guide channel.

30. The optical recording medium of claim 28, wherein said pre-groove is an addressing channel.

31. The optical recording medium of claim 23, wherein pits are produced in said radiation-sensitive organic thin film by irradiating with radiation.

32. The electrophotographic photosensitive member of claim 16, wherein said photoconductive material is an inorganic photoconductive material.

33. The electrophotographic photosensitive member of claim 32, wherein said inorganic photoconductive material is at least one material selected from the group consisting of selenium, cadmium sulfide, and zinc oxide.

34. The electrophotographic photosensitive member of claim 32, wherein said inorganic photoconductive material is zinc oxide.

* * * * *

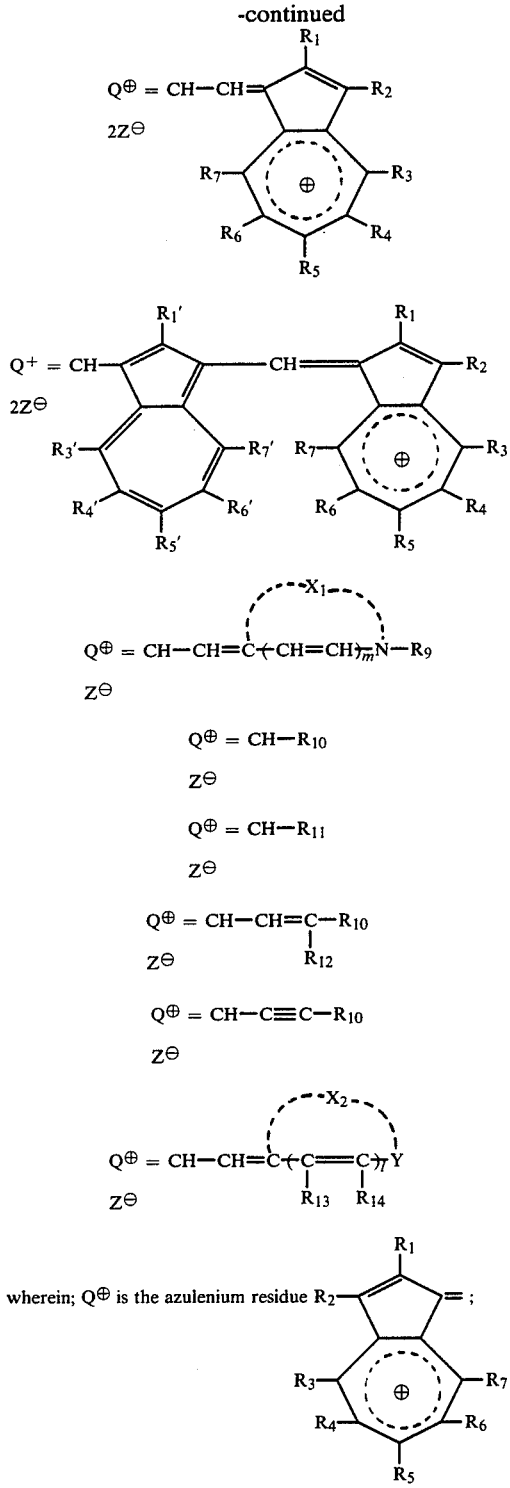

each of $R_1$, $R_2$, $R_3$, $R_4$, $R_5$, $R_6$, and $R_7$ is hydrogen, halogen, or an organic monovalent residue, where at least one of the combinations ($R_1$ and $R_2$), ($R_3$ and $R_4$), ($R_4$ and $R_5$), ($R_5$ and $R_6$), and ($R_6$ and $R_7$) may form a substituted or unsubstituted aromatic ring;

each of $R_1'$, $R_2'$, $R_3'$, $R_4'$, $R_5'$, $R_6'$, and $R_7'$ is hydrogen, halogen, or an organic monovalent residue, where at least one of the combinations ($R_1'$ and $R_2'$), ($R_3'$ and $R_4'$), ($R_4'$ and $R_5'$), ($R_5'$ and $R_6'$), and ($R_6'$ and $R_7'$) may form a substituted or unsubstituted aromatic ring;

$Z^\ominus$ is an anionic residue;

$R_8$ is hydrogen, nitro, cyano, alkyl, or aryl;

$R_9$ is substituted or unsubstituted alkyl, substituted or unsubstituted aryl, cycloalkyl, alkenyl, or substituted or unsubstituted aralkyl;

$R_{10}$ is substituted or unsubstituted aryl;

$R_{11}$ is a monovalent heterocyclic residue;

$R_{12}$ is hydrogen, alkyl, or substituted or unsubstituted aryl;

$R_{13}$ and $R_{14}$ each are hydrogen, alkyl, alkoxy, substituted or unsubstituted aryl, substituted or unsubstituted styryl, ring-substituted or unsubstituted 4-phenyl-1,3-butadienyl, or a substituted or unsubstituted heterocyclic residue;

$X_1$ is a nonmetal atomic group necessary to complete a nitrogen-containing heterocyclic residue;

$X_2$ is an atomic group necessary to complete pyrane, thiopyrane, selenopyrane, benzopyrane, benzothiopyrane, benzoselenopyrane, naphthopyrane, naphthothiopyrane, or naphthoselenopyrane ring substituted or unsubstituted;

Y is sulfur, oxygen, or selenium;

n is an integer of 0, 1, or 2; and m is an integer of 0 or 1.

l is an integer of 0 or 1.

5. The electrophotographic photosensitive member of claim 3, wherein said radiation-sensitive organic thin film further comprises a binder.

6. The electrophotographic photosensitive member of claim 3, wherein said radiation-sensitive organic thin film is contained in a charge generation layer and further comprising a charge transport layer in contact with said charge generation layer.

7. The electrophotographic photosensitive member of claim 6, wherein said charge generation layer further comprises a binder.

8. The electrophotographic photosensitive member of claim 6, wherein said charge transport layer is formed on the opposite side of said charge generation layer from said conductive substrate.

9. The electrophotographic photosensitive member of claim 8, which has an intermediate layer between said charge generation layer and said conductive substrate.

10. The electrophotographic photosensitive member of claim 6, wherein said charge transport layer comprises a hole-transporting material and a binder.

11. The electrophotographic photosensitive member of claim 10, wherein said hole-transporting material is at least one compound selected from the group consisting of aromatic condensed ring compounds, hydrazones, pyrazolines, oxazoles, thiazoles, triaryl methanes, polyarylalkanes, polyphenylamines, and organic photoconductive polymers.

12. The electrophotographic photosensitive member of claim 11, wherein said hole-transporting material is a hydrazone.

13. The electrophotographic photosensitive member of claim 6, wherein said charge transport layer is a thin film of amorphous silicon.

14. The electrophotographic photosensitive member of claim 6, wherein said charge transport layer comprises a binder and a material selected from selenium, cadmium sulfide, and zinc oxide.

15. The electrophotographic photosensitive member of claim 6, wherein said charge transport layer is a thin film of selenium.

16. The electrophotographic photosensitive member of claim 3, where said compound having at least one nucleus of azulenium salt is a sensitizer for a photoconductive material.

17. The electrophotographic photosensitive member of claim 16, wherein said photoconductive material is at least one compound selected from the group consisting of aromatic condensed ring compounds, hydrazones, pyrazolines, oxazoles, thiazoles, triarylmethanes, polyarylalkanes, polyphenylamines, and organic photoconductive polymers.

18. The electrophotographic photosensitive member of claim 3, wherein said radiation is electromagnetic radiation having wavelengths belonging to the spectrum from visible light to infrared.

19. The electrophotographic photosensitive member of claim 18, wherein said radiation is electromagnetic radiation having wavelengths belonging to the spectrum from near-infrared to infrared.

20. The electrophotographic photosensitive member of claim 18, wherein said radiation is in the form of a laser beam.

21. The electrophotographic photosensitive member of claim 19, wherein said radiation is in the form of a laser beam.

22. The electrophotographic photosensitive member of claim 20, wherein said laser beam is emitted from a semiconductor laser.

23. An optical recording medium having a radiation-sensitive organic thin film which comprises a radiation-sensitive compound having at least one nucleus of an azulenium salt; said compound represented by the following general formula I, II or III:

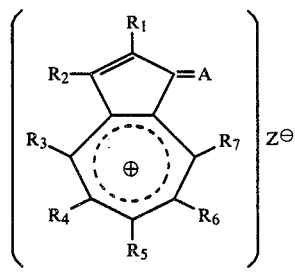

[I]

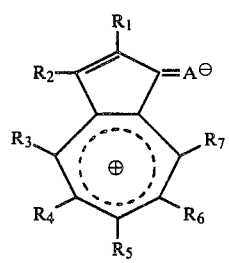

[II]

-continued

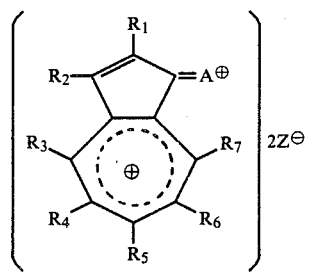

[III]

wherein; each of $R_1$, $R_2$, $R_3$, $R_4$, $R_5$, $R_6$, and $R_7$ is hydrogen, halogen, or an organic monovalent residue, where at least one of the combinations ($R_1$ and $R_2$), ($R_3$ and $R_4$), ($R_4$ and $R_5$), ($R_5$ and $R_6$), and ($R_6$ and $R_7$) may form a substituted or unsubstituted aromatic ring; A is an organic divalent residue attached through a double bond to the azulenium nucleus; and $Z^{\ominus}$ is an anionic residue; optical properties of said film being changeable by irradiating with radiation.

24. The optical recording medium of claim 23, wherein said compound having at least one nucleus of an azulenium salt is represented by one of the following general formulae (1)–(11):

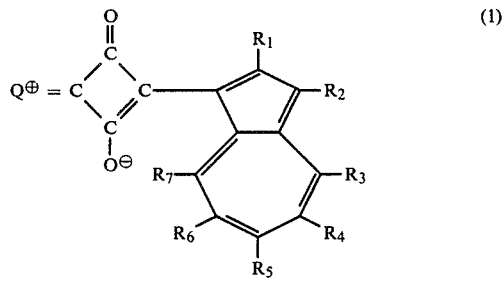

(1)

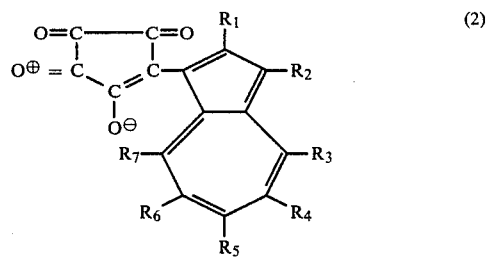

(2)

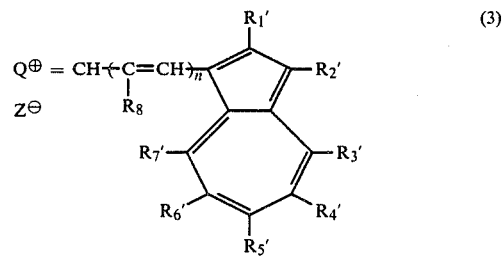

(3)

UNITED STATES PATENT AND TRADEMARK OFFICE
CERTIFICATE OF CORRECTION

PATENT NO. : 4,548,886
DATED : October 22, 1985
INVENTOR(S) : Katagiri, et al.

It is certified that error appears in the above-identified patent and that said Letters Patent is hereby corrected as shown below:

Column 1, line 13, after "as" insert --a--.
Column 4, formula (I) should be

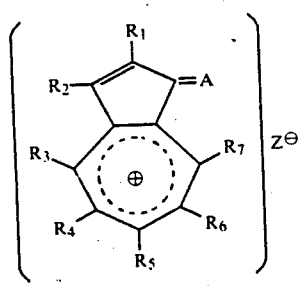

Column 7, line 2, "nitrogencontaining" should be --nitrogen-containing--.
Column 14, in formula (52), "M" should be --N--.
Column 21, line 30, "2,76" should be --2.76--.
Column 21, line 30, after "N2.71" insert --,--.
Column 23, line 49, delete "the" (second occurrence).
Column 25, line 39, "combination" to --combinations--.
Column 27, line 57, "homogenious" should be --homogeneous--.
Column 28, line 37, "pregrooves" should be --pre-grooves--.

Signed and Sealed this

Twentieth Day of January, 1987

Attest:

DONALD J. QUIGG

Attesting Officer      Commissioner of Patents and Trademarks

UNITED STATES PATENT AND TRADEMARK OFFICE
CERTIFICATE OF CORRECTION

PATENT NO. : 4,548,886
DATED : October 22, 1985
INVENTOR(S) : Katagiri, et al.

It is certified that error appears in the above-identified patent and that said Letters Patent is hereby corrected as shown below:

Column 1, line 13, after "as" insert --a--.
Column 4, formula (I) should be

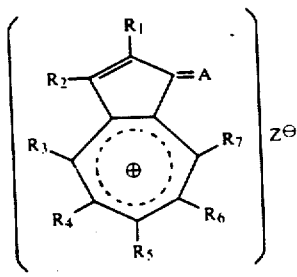

Column 7, line 2, "nitrogencontaining" should be --nitrogen-containing--.
Column 14, in formula (52), "M" should be --N--.
Column 21, line 30, "2,76" should be --2.76--.
Column 21, line 30, after "N2.71" insert --,--.
Column 23, line 49, delete "the" (second occurrence).
Column 25, line 39, "combination" to --combinations--.
Column 27, line 57, "homogenious" should be --homogeneous--.
Column 28, line 37, "pregrooves" should be --pre-grooves--.

Signed and Sealed this

Twentieth Day of January, 1987

Attest:

DONALD J. QUIGG

Attesting Officer        Commissioner of Patents and Trademarks